United States Patent [19]

Furutachi

[11] Patent Number: 4,910,124
[45] Date of Patent: Mar. 20, 1990

[54] COLOR IMAGE-FORMING PROCESS

[75] Inventor: Nobuo Furutachi, Kanagawa, Japan

[73] Assignee: Fuji Photo Film Co., Ltd., Kanagawa, Japan

[21] Appl. No.: 275,616

[22] Filed: Nov. 25, 1988

Related U.S. Application Data

[63] Continuation of Ser. No. 13,513, Feb. 2, 1987, abandoned.

[30] Foreign Application Priority Data

Feb. 12, 1986 [JP] Japan .................................. 61-28709

[51] Int. Cl.$^4$ .......................... G03C 5/26; G03C 7/30; G03C 7/38
[52] U.S. Cl. ..................................... 430/387; 430/380; 430/399; 430/558
[58] Field of Search ......................... 430/558, 387, 380

[56] References Cited

U.S. PATENT DOCUMENTS

| | | | |
|---|---|---|---|
| 4,500,630 | 2/1985 | Sato et al. | 430/387 |
| 4,595,650 | 6/1986 | Furutach et al. | 430/387 |
| 4,618,573 | 10/1986 | Okamura et al. | 430/558 |
| 4,665,015 | 5/1987 | Iijima et al. | 430/558 |
| 4,675,275 | 6/1987 | Nishijima et al. | 430/558 |
| 4,684,603 | 8/1987 | Nishijima et al. | 430/558 |

FOREIGN PATENT DOCUMENTS 158446 8/1985 Japan .
30250 2/1987 Japan .

OTHER PUBLICATIONS

EP-A-0 119860 (Fuji Photo Film).

Primary Examiner—Paul R. Michl
Assistant Examiner—Mark R. Buscher
Attorney, Agent, or Firm—Sughrue, Mion, Zinn, Macpeak & Seas

[57] ABSTRACT

A color image-forming process is described, which comprises developing with a color developing solution containing an aromatic primary amine developing agent a silver halide color photographic material containing at least on pyrazoloazole coupler represented by formula (Ia) or (Ib)

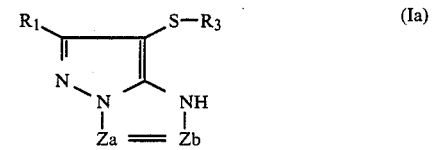

(Ia)

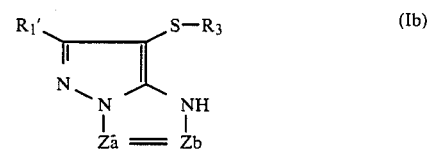

(Ib)

wherein $R_1$, $R_1'$, $R_3$, $Z_a$, and $Z_b$ are defined in the specification. The image-forming process of the invention provides a silver halide color photographic material having high maximum color density, showing high coloring speed, and forming color images excellent in fastness. Further, the process of the invention can reveal the above-described excellent properties using a color developing solution containing substantially no benzyl alcohol.

13 Claims, No Drawings

COLOR IMAGE-FORMING PROCESS

This is a continuation of application Ser. No. 013,513, filed Feb. 2, 1987, now abandoned.

FIELD OF THE INVENTION

This invention relates to an image-forming process for silver halide color photographic materials, and more specifically to an image-forming process for silver halide color photographic materials providing high maximum color density, showing high coloring speed, and forming color images excellent in fastness.

BACKGROUND OF THE INVENTION

It is well known that couplers react with an oxidized aromatic primary amine color developing agent using light-exposed silver halide as an oxidizing agent to form dyes such as indophenol dyes, indoaniline dyes, indamine dyes, azomethine dyes, phenoxazine dyes, phenazine dyes, or analogous dyes, whereby color images are formed.

In these couplers, 5-pyrazolone series couplers, cyanoacetophenone series couplers, indazolone series couplers, pyrazolobenzimidazole series couplers, and pyrazolotriazole series couplers are used for forming magenta color images.

The couplers which have hitherto been most widely used as magenta color image-forming couplers (hereinafter also more briefly referred to as "magenta couplers") and have variously investigated are 5-pyrazolone series couplers. However, it is known that these exists an undesired absorption having a yellow component near 430 nm in dyes formed from 5-pyrazoline series couplers, which causes the formation of color stains.

As magenta color image-forming couplers reducing the yellow component of the dyes formed, pyrazolobenzimidazole couplers have been described, e.g., in British Patent 1,047,612, and pyrazolo[5,1-c]-1,2,4-triazole couplers have been described, e.g., in U.S. Pat. No. 3,725,067.

However, the magenta couplers described in the aforesaid patents also have some undesirable properties. Particularly, when such couplers are mixed with a silver halide emulsion as a dispersion in a hydrophilic protective colloid such as gelatin, unsatisfactory color images are formed, the solubility of the couplers in high-boiling organic solvents is low, the couplers cannot be easily prepared, the couplers show relatively low coupling activity by use of usual developing solutions, and dyes formed from the couplers have very low light fastness.

Recently, imidazopyrazole couplers have been disclosed, e.g., in Japanese Patent Application (OPI) No. 162548/84 (the term "OPI" as used herein means an "unexamined published application"), 1H-pyrazolo[1,5-b]-1,2,4-triazole couplers have been disclosed in Japanese Patent Application (OPI) No. 171956/84, and pyrazolotetrazole couplers have been disclosed in Japanese Patent Application (OPI) No. 33552/85, for solving the aforesaid problems. Also, the magenta couplers improving the coloring property by introducing a specific substituent to the pyrazole[5,1-c]-1,2,4-triazole are known, as described, e.g., in Japanese Patent Application (OPI) No. 98438/85. Also, 1H-pyrazolo[3,2-c]-s-triazole type couplers have been disclosed in Japanese Patent Application (OPI) No. 125743/84.

However, even when the couplers described above are used, they are not entirely satisfactory from the viewpoint of obtaining high color density, high coloring speed, and also high fastness of dye images formed. Furthermore, there is a remarkable different in attainable maximum density between the case of developing a reflective color photographic material containing the aforesaid magenta coupler with a color developing solution containing benzyl alcohol and the case of developing the color photographic material with a color developing solution that does not contain benzyl alcohol, and particularly, the problem that developing with a color developing solution containing no benzyl alcohol gives low coloring.

SUMMARY OF THE INVENTION

An object of this invention is to solve the aforesaid problems and to provide a color image-forming process capable of providing magenta color images having high fastness and high color density at a high coloring speed.

It has now been discovered that the above-described object can be attained by the invention as set forth hereinbelow.

That is, in one embodiment, the present invention is directed to a color image-forming process which comprises developing with a color developing solution containing an aromatic primary amine developing agent a silver halide color photographic material containing at least one pyrazoloazole coupler represented by formula (Ia)

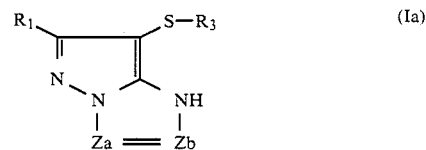

wherein Za and Zb each represents —CH=,

or —N=; $R_1$ and $R_2$ each represents a substituent, at least one of said $R_1$ and $R_2$ representing a group bonding to the pyrazoloazole nucleus by a nitrogen atom, oxygen atom, or sulfur atom thereof, provided that $R_1$ does not represent an alkoxy group, an aryloxy group, a heterocyclic group, or a divalent group thereof; and $R_3$ represents an alkyl group, an aralkyl group, a cycloalkyl group, an aryl group, or a heterocyclic group, each containing at least 12 carbon atoms.

In another embodiment, the present invention is directed to a color image-forming process which comprises developing with a color developing solution containing an aromatic primary amine developing agent and having substantially no benzyl alcohol a silver halide color photographic material containing a reflective support having thereon at least one silver halide emulsion layer associated with at least one pyrazoloazole coupler represented by formula (Ib)

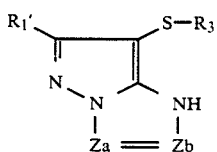 (Ib)

wherein Za and Zb each represents —CH═,

or —N═; $R_1'$ and $R_2$ each represents a substituent; at least one of said $R_1'$ and $R_2$ represents a group bonded to the pyrazoloazole nucleus by a nitrogen atom, oxygen atom, or sulfur atom thereof; and $R_3$ represents an alkyl group, an aralkyl group, a cycloalkyl group, an aryl group, or a heterocyclic group, each containing at least 12 carbon atoms.

DETAILED DESCRIPTION OF THE INVENTION

The magenta couplers for use in this invention represented by formula (Ia) or (Ib) described above are described below in further detail.

In formula (Ia) or (Ib) described above, at least one of $R_1$ and $R_1'$ and $R_2$ represents a group bonded to the pyrazoloazole nucleus of the coupler by a nitrogen atom, oxygen atom, or sulfur atom thereof.

Examples of the group bonded by a nitrogen atom thereof are an acylamino group (e.g., an acetylamino group, a benzamido group, a 2,4-di-tert-amylphenoxyacetamido group, a 2,4-dichlorobenzamido group, etc.), an alkoxycarbonylamino group (e.g., a methoxycarbonylamino group, a propoxycarbonylamino group, a t-butoxycarbonylamino group, etc.), an aryloxycarbonylamino group (e.g., a phenoxycarbonylamino group, etc.), a sulfonamido group (e.g., a methanesulfonamido group, an octanesulfonamido group, a benzenesulfonamido group, a 4-dodecyloxybenzenesulfonamido group, etc.), an anilino group (e.g., a phenylamino group, a 2-chloroanilino group, a 2-chloro-tetradecanamidoanilino group, etc.), a ureido group (e.g., an N-methylureido group, an N-butylureido group, an N-phenylureido group, an N,N-dibutylureido group, etc.), a sulfamoylamino group (e.g., an N,N-diethylsulfamoylamino group, an N-phenylsulfamoyl group, etc.), an amino group (e.g., an unsubstituted amino group, an N-methylamino group, an N,N-diethylamino group, an N,N-dibutylamino group, etc.), etc.

Examples of the group bonded by an oxygen atom thereof are an alkoxy group (e.g., a methoxy group, an ethoxy group, a butoxy group, an isopropoxy group, a methoxyethoxy group, a 2,2,2-trifluoroethoxy group, a 3,3,3-trifluoropropoxy group, a 2-chloroethoxy group, a 2-cyanoethoxy group, a 2-butanesulfonylethoxy group, etc.), an aryloxy group (e.g., a phenoxy group, a 4-methoxyphenoxy group, a 4-ethoxyphenoxy group, a 2,4-dichlorophenoxy group, a 4-(2-ethylhexanamido)phenoxy group, etc.), a silyloxy group (e.g., a trimethylsilyloxy group, a dimethylphenylsilyloxy group, a dimethyl-tert-butylsilyloxy group, etc.), a heterocyclic oxy group (e.g., a tetrahydropyranyloxy group, a 3-pyridyloxy group, a 2-(1,3-benzoimidazolyl)oxy group, etc.), etc.

Examples of the group bonded by a sulfur atom thereof are an alkylthio group (e.g., a methylthio group, an ethylthio group, a butylthio group, a 3-(4-aminophenyl)propylthio group, a benzylthio group, a 4-aminobenzylthio group, a 3-[4-(4-dodecyloxyphenyl)-sulfonamidophenyl]propylthio group, a 4-(2-butoxy-5-tert-octylphenylsulfonamido)benzylthio group, etc.), an arylthio group (e.g., a phenylthio group, a 2-naphthylthio group, a 2,5-dichlorophenylthio group, a 4-dodecylphenylthio group, a 2-butoxy-5-tert-octylphenylthio group, etc.), a heterocyclic thio group (e.g., a 2-pyridylthio group, a 2-(1,2-benzoxazolyl)thio group, a 1-hexadecyl-1,2,3,4-tetrazolyl-5-thio group, a 1-(3-N-octadecylcarbamoyl)phenyl-1,2,3,4-tetrazolyl-5-thio group, etc.), etc.

Also, specific examples of substituents represented by $R_1$ or $R_1'$ or $R_2$ other than the groups bonded by a nitrogen atom, sulfur atom, or oxygen atom thereof are a hydrogen atom, a halogen atom (e.g., a chlorine atom, a bromine atom, a fluorine atom, etc.), an alkyl group (e.g., a methyl group, a propyl group, a t-butyl group, an isopropyl group, a trifluoromethyl group, a benzyl group, a 3-(4-aminophenyl)propyl group, an allyl group, a 2-dodecyloxyethyl group, a 3-phenoxypropyl group, a 2-hexylsulfonylethyl group, a 3-[4-(4-dodecyloxyphenyl)sulfonamdiophenyl]propyl group, a 1-methyl-2-[(2-octyloxy-5-tert-octylphenyl)sulfonamidophenyl]ethyl group, a 1-methyl-2-[octyloxy-5-(2-octyloxy-5-tertoctylphenylsulfonamido)phenylsulfonamido]ethyl group, a 2-[2-octyloxy-5-(2-octyloxy-5-tert-octylphenylsulfonamido)phenylsulfonamido]ethyl group, etc.), a heterocyclic group (e.g., a 2-furyl group, a 2-thienyl group, a 2-pyrimidinyl group, a 2-benzothiazolyl group, etc.), a cyano group, etc.

$R_3$ represents an alkyl group having at least 12 carbon atoms (e.g., a dodecyl group, a hexadecyl group, a dodecyloxycarbonylmethyl group, a 1-dodecyloxycarbonylpropyl group, a 1-(dodecyloxycarbonyl)-dodecyloxycarbonylmethyl group, etc.), an aralkyl group having at least 12 carbon atoms (e.g., a 4-tetradecanamidobenzyl group, a 4-dodecyloxybenzyl group, a 2-chloro-4-decanamidobenzyl group, a 4-hexadecyloxycarbonylbenzyl group, a 2-(4-dodecanamidophenyl)ethyl group, etc.), a cycloalkyl group having at least 12 carbon atoms (e.g., a 4-dodecylcyclohexyl group, a 4,4-dihexylcyclohexyl group, a 3-methyl-4-dodecylcyclohexyl group, a 3,4-dioctyloxycyclopentyl group, etc.), a heterocyclic group having at least 12 carbon atoms (e.g., a 1-octadecyl-1,2,3,4-tetrazol-5-yl group, a 1-(3-N-dodecylcarbamoylphenyl)-1,2,3,4-tetrazol-5-yl group, a 3-(4-dodecyloxyphenyl)-1,2,4-triazol-5-yl group, a 1-dodecyl-1,3-benzodiazol-2-yl group, etc.), or an aryl group having at least 12 carbon atoms (e.g., a 3-N-octadecylcarbamoylphenyl group, a 4-dodecylphenyl group, a 4-tetradecyloxyphenyl group, a 3-hexadecyloxyphenyl group, a 3,5-bis(dodecyloxycarbonyl)phenyl grup, a 4-(4-dodecyloxypheny)sulfonamidophenyl group, a 2-chloro-5-tetradecanamidophenyl group, a 2-methyl-5-tert-octylphenyl group, a 2-methyl-5-tetradecyloxyphenyl group, a 2-methyl-4-dodecyloxyphenyl group,

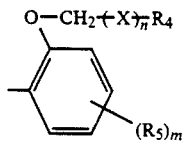

(wherein $R_4$, $R_5$, X, m, and n are explained below in regard to formula (IIa) or (IIb) described hereunder), etc.).

Also, the group, $-S-R_3$ is split off from the coupler of formula (Ia) or (Ib) in the course of the coupling reaction, and since if the group thus split off is dissolved in the color developing solution, it causes a development inhibiting action, it is preferred for preventing the dissolution of the group that the carbon atom number of $R_3$ is at least 12.

Of the compounds represented by formula (Ia) or (Ib) described above, compounds represented by formula (IIa) or (IIb) shown below are particularly preferred.

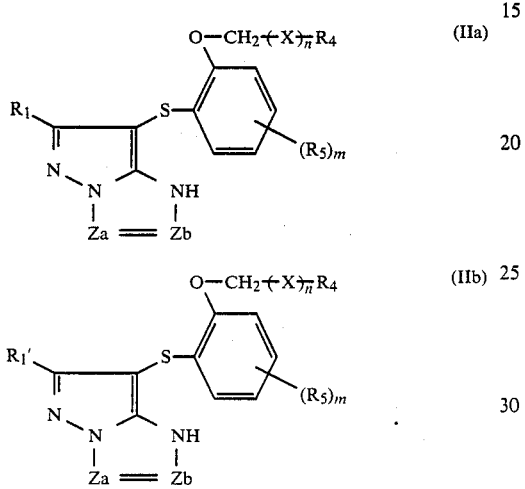

wherein $R_1$, $R_1'$, Za, and Zb have the same meanings as defined above for formula (Ia) or (Ib); X represents $-CH_2-O-$, $-CH_2O-CH_2CH_2O-$, $-CH_2SO_2-$, $-CH_2CH_2CH_2SO_2NH-$, $-CH_2CH_2CH_2SO_2NHCH_2CH_2O-$, $-CH_2CH_2CONH-$, $-CH_2-COO-$, $-CH_2CONH-$, $-CH_2CH_2CH_2CONH-$, $-CH_2CH_2SO_2-$, $-CH_2CH_2SO_2NH-$, $-CH_2CH_2NHSO_2-$, $-CH_2NHSO_2-$, $-CH_2NHCO-$, $-CH_2CH_2NHCO-$,

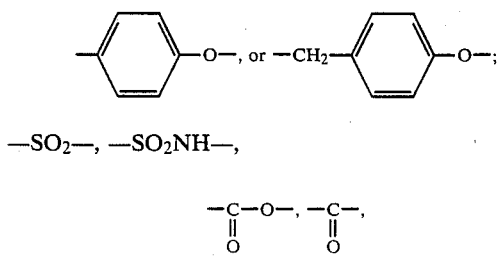

$-SO_2-$, $-SO_2NH-$, $-\underset{\underset{O}{\|}}{C}-O-$, $-\underset{\underset{O}{\|}}{C}-$, $R_4$ represents an alkyl group or an aryl group; $R_5$ represents a halogen atom, an alkoxy group, an alkyl group, an aryl group, a hydroxyl group, an amino group, an N-alkylamino group, an N,N-dialkylamino group, an N-anilino group, an acrylamino group, a ureido group, an alkoxycarbonylamino group, an imido group, a sulfonamido group, a sulfamoylamino group, an alkoxycarbonyl group, a carbamoyl group, an acyl group, a cyano group, or an alkylthio group; n represents 0 or 1; m represents 0 or an integer of 1 to 4; and when m is 2 or more, said $R_5$ groups may be the same or different. As specific examples of the alkyl group, the aryl group, etc. represented by $R_4$ or $R_5$, those of the alkyl group, the aryl group, etc., as enumerated for formula (Ia) or (Ib) described above can be exemplified.

Particularly preferred compounds of the compounds represented by formula (IIa) or (IIb) above are represented by formula (IIIa) or (IIIb) and (IVa) or (IVb).

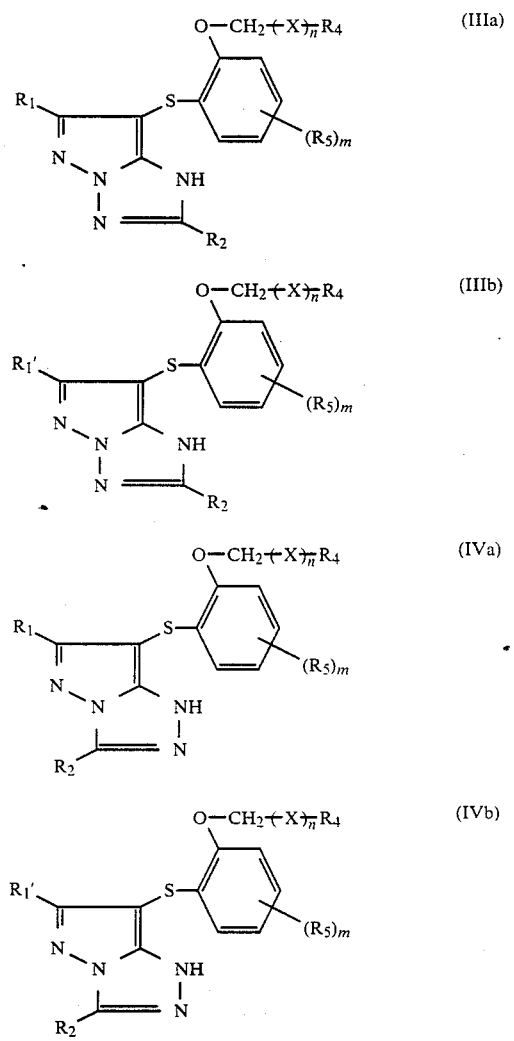

wherein $R_1$, $R_1'$, $R_2$, $R_4$, $R_5$, X, n, and m have the same meanings as defined above in regard to formulae (Ia) or (Ib) and (IIa) or (IIb).

In the particularly preferred compounds represented by formula (IIIa) or (IIIb), $R_1$ is a ureido group, or $R_1'$ is an alkoxy group, a ureido group, or an aryloxy group, and $R_2$ is an alkyl group.

Also, in the particularly preferred compounds represented by formula (IVa) or (IVb), $R_1$ is an alkyl group, or $R_1'$ is an alkyl group or an alkoxy group, and $R_2$ is an alkylthio group. In more particularly preferred compounds of formula (IIIa) or (IIIb) or (IVa) or (VIb), n is 0, $R_4$ is an unsubstituted alkyl group having from 1 to 7 carbon atoms, m is 1, and $R_5$ is an unsubstituted alkyl group.

Furthermore, the couplers represented by the aforesaid formulae may form a bis-compound having two dye-forming sites by $R_1$ or $R_1'$ or $R_2$, and may also be a homopolymer or a copolymer having a recurring unit containing the compound moiety represented by formula (Ia) or (Ib) described above.

Specific example compounds of the magenta couplers of this invention represented by the aforesaid formulae are illustrated below, but the compounds for use in this invention are not limited thereto.
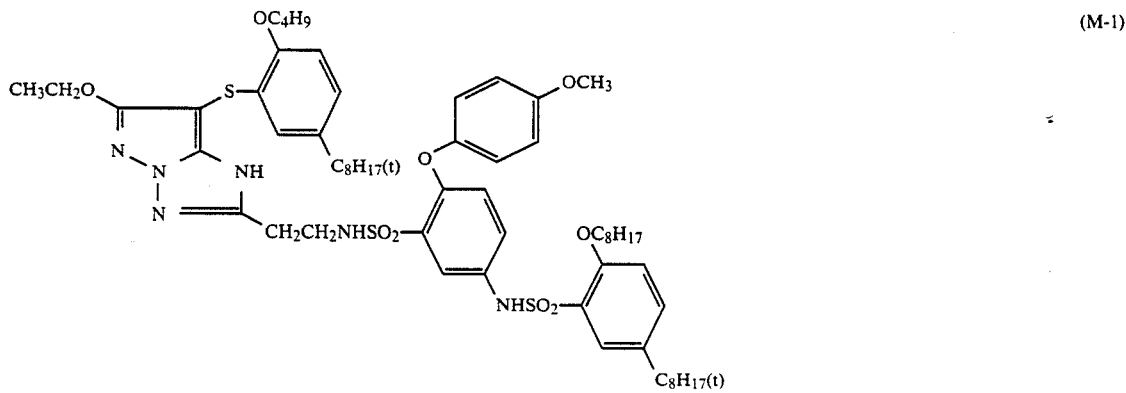
(M-1)
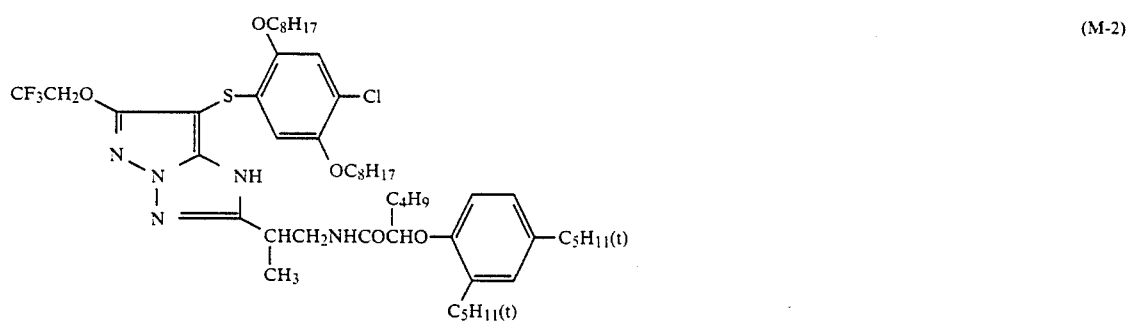
(M-2)
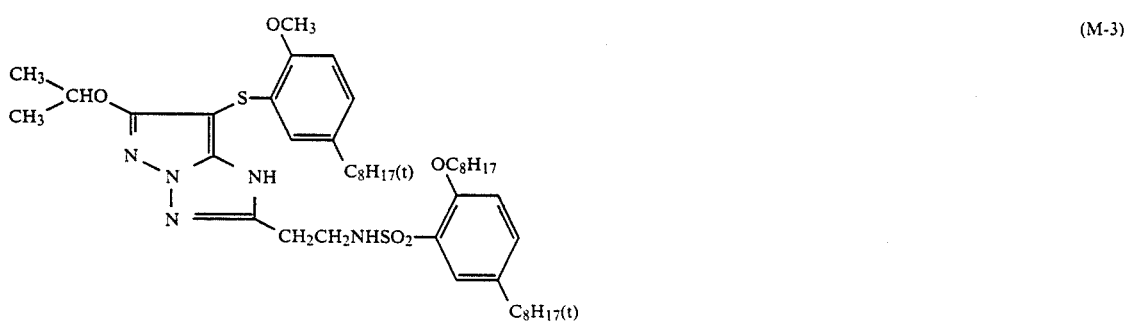
(M-3)
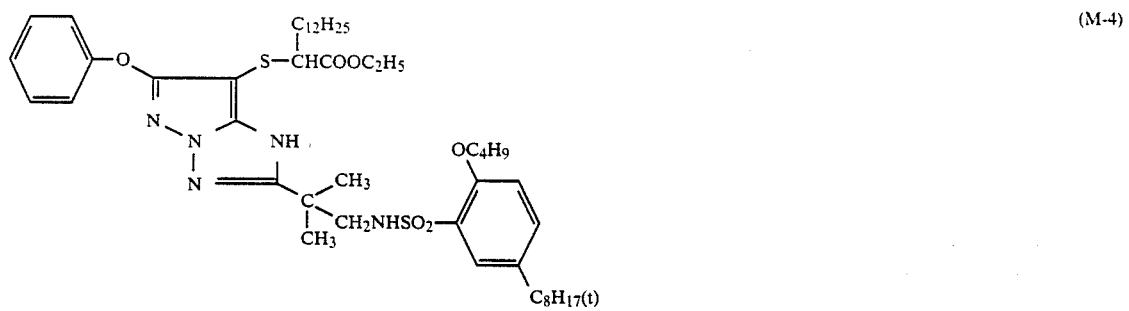
(M-4)

-continued
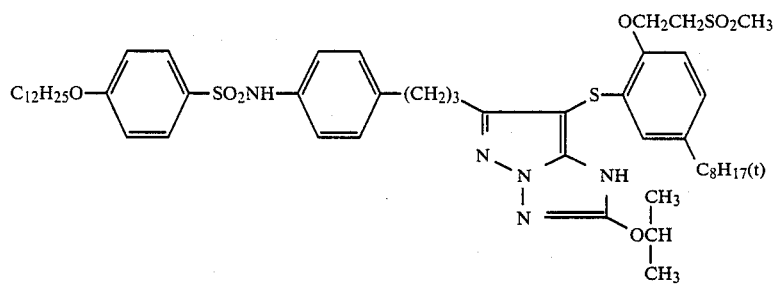
(M-5)
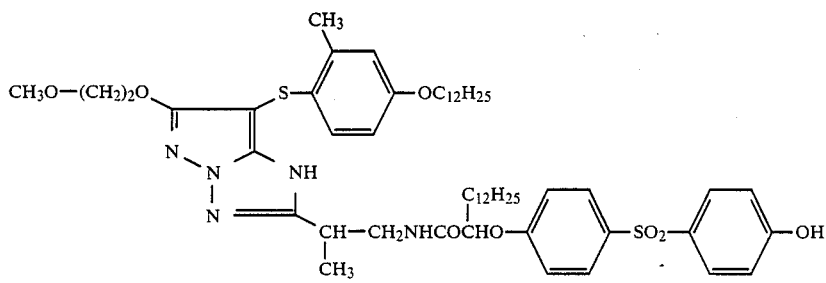
(M-6)
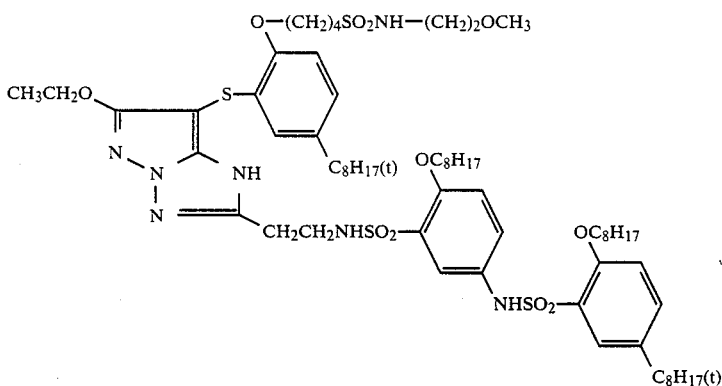
(M-7)
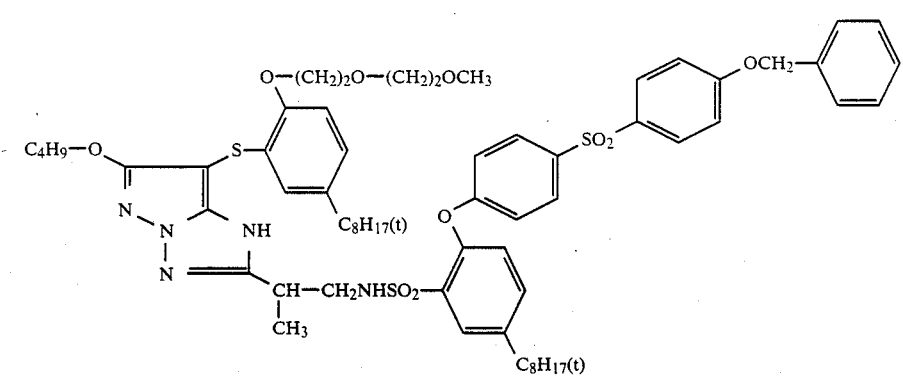
(M-8)

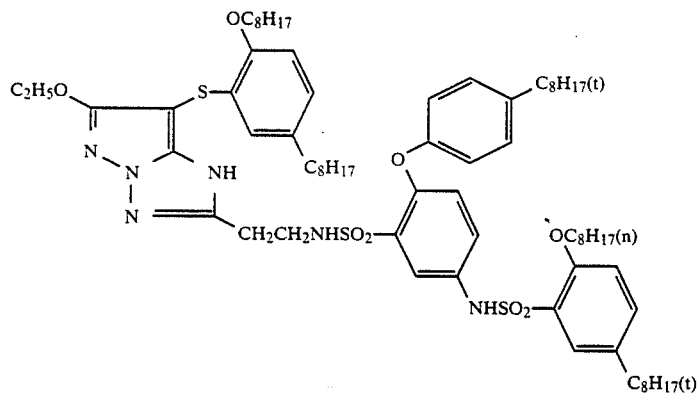
(M-9)
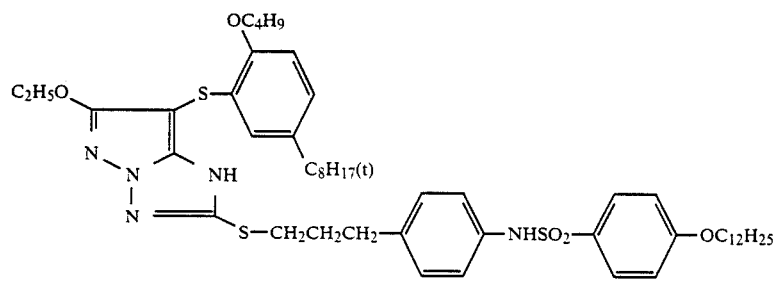
(M-10)
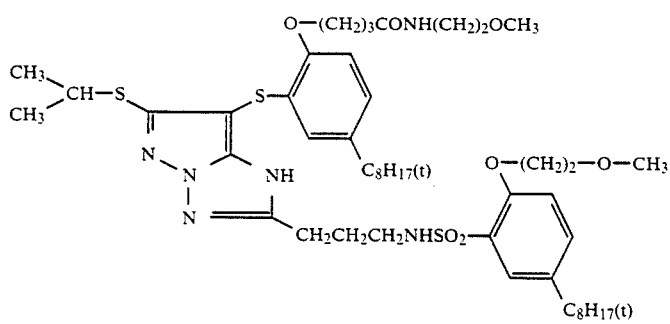
(M-11)
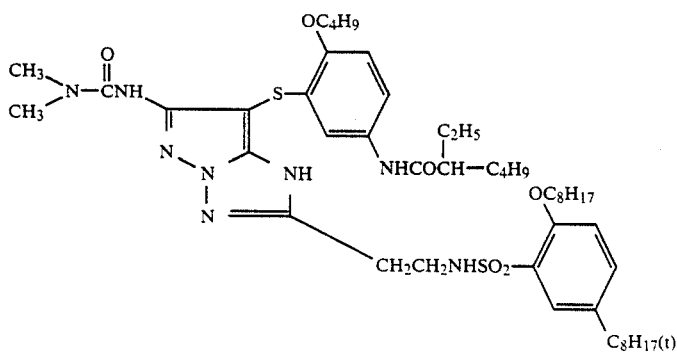
(M-12)
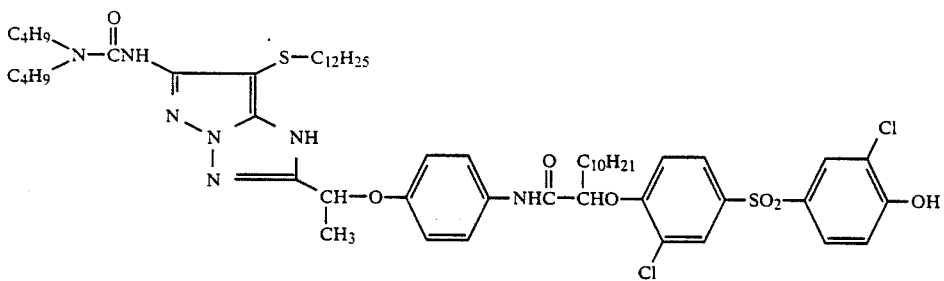
(M-13)

-continued
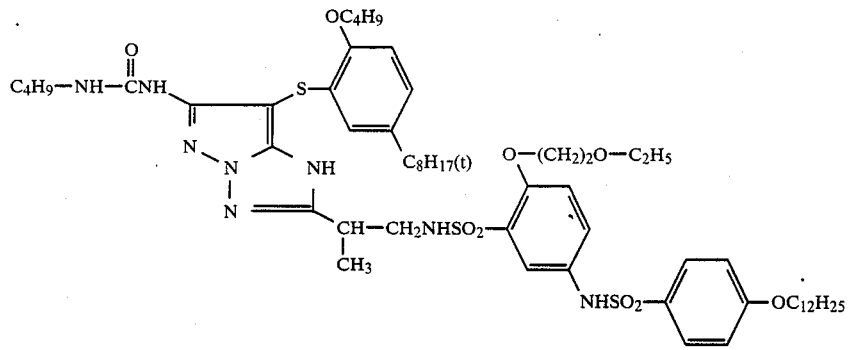
(M-14)
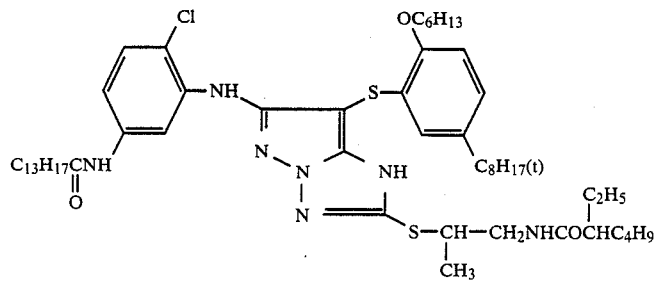
(M-15)
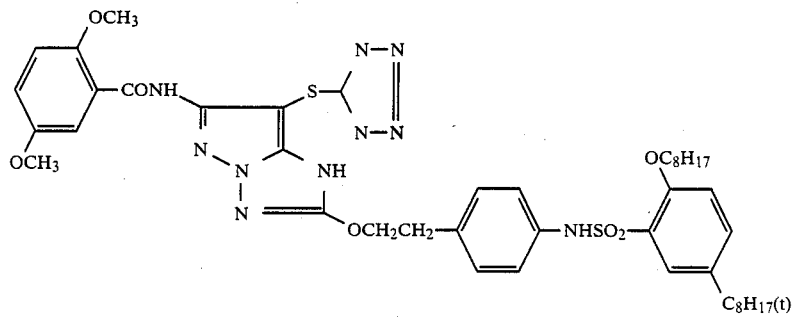
(M-16)
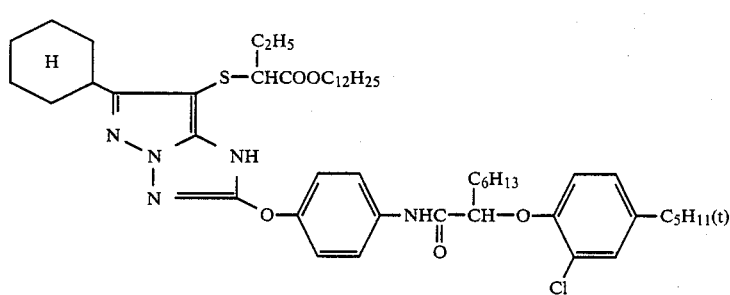
(M-17)
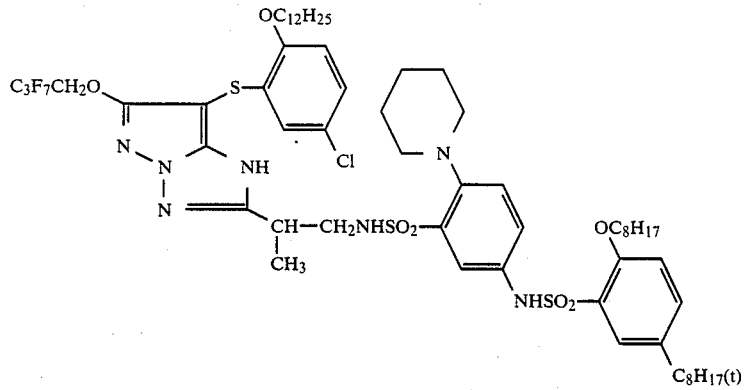
(M-18)

(M-19)
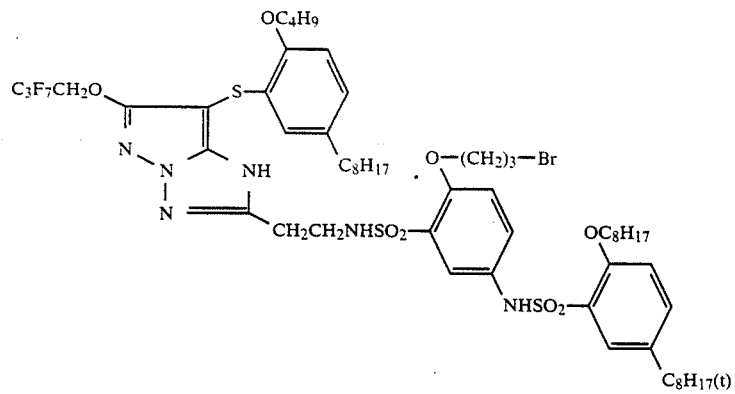
(M-20)
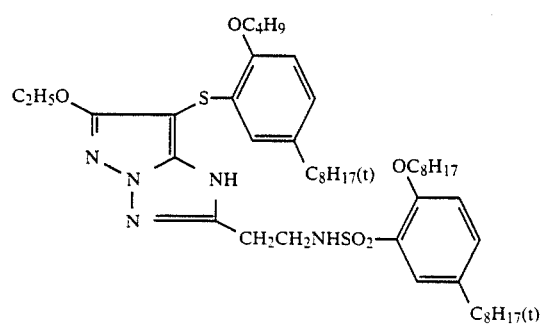
(M-21)
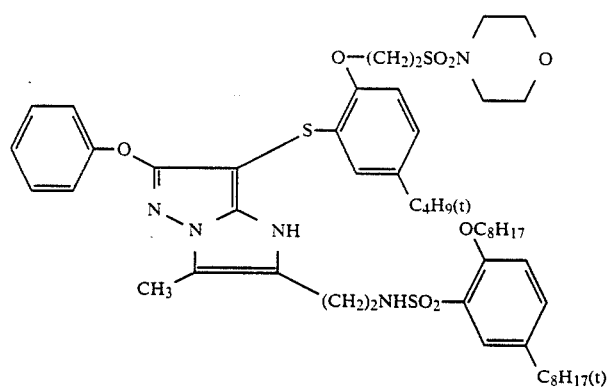
(M-22)
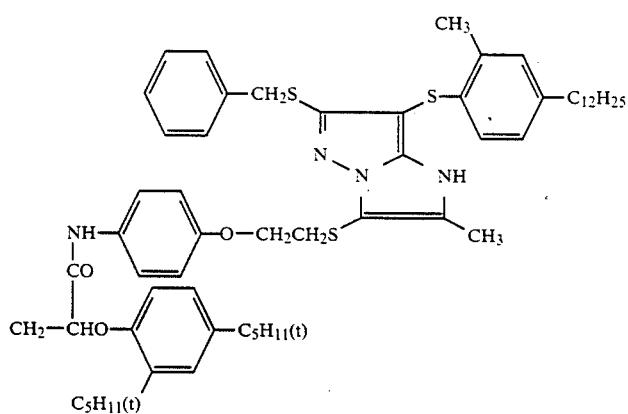

-continued
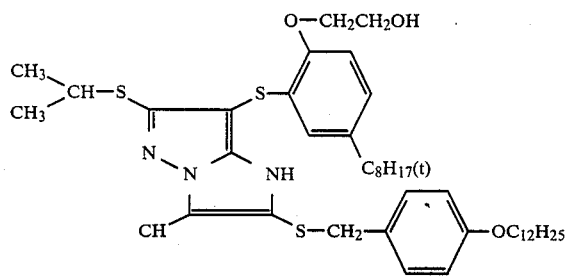
(M-23)
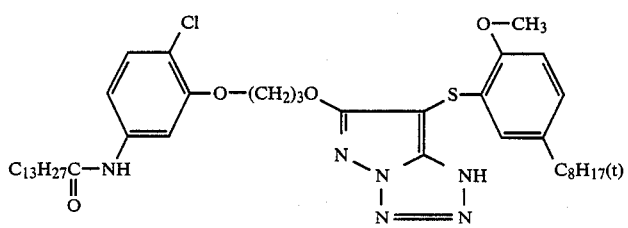
(M-24)
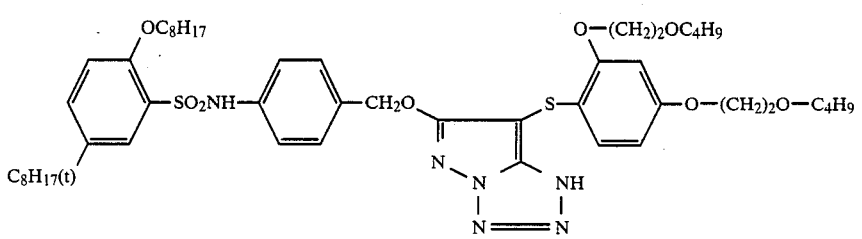
(M-25)
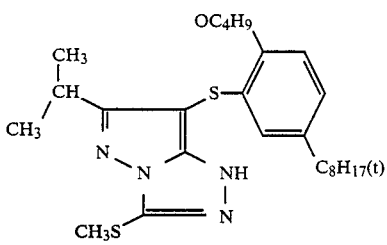
(M-26)
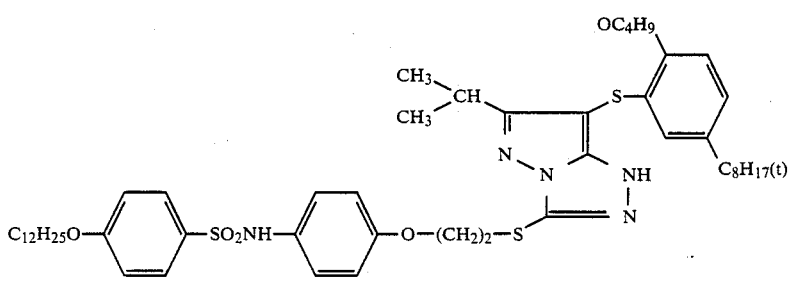
(M-27)
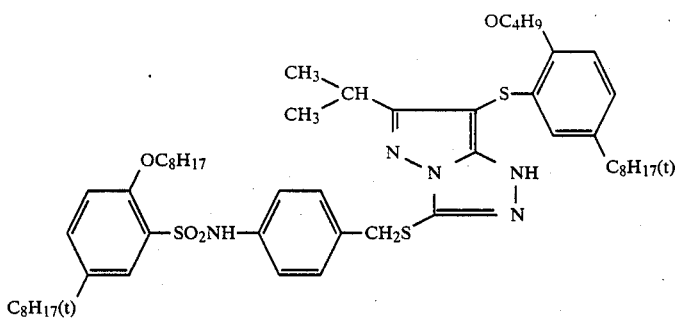
(M-28)

-continued
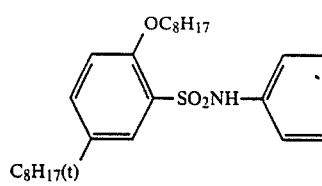 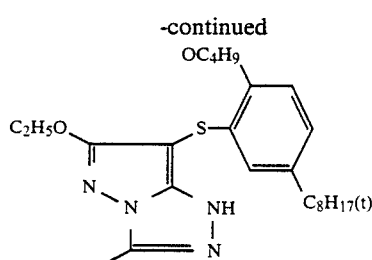 (M-29)
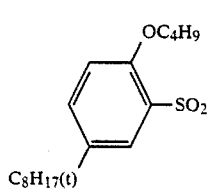 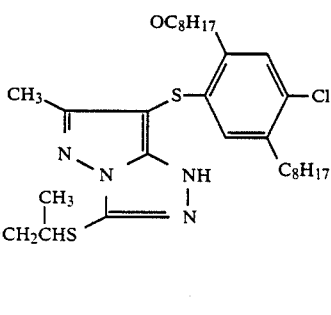 (M-30)
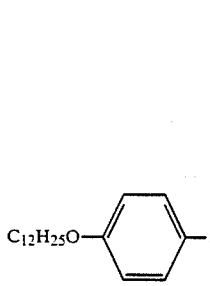 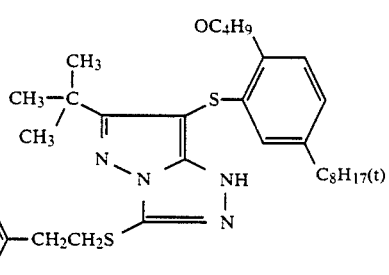 (M-31)
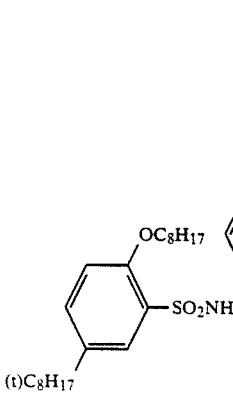 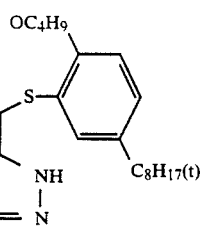 (M-32)
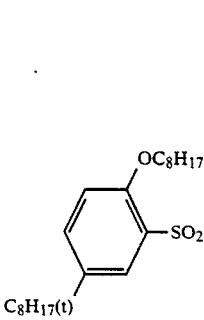 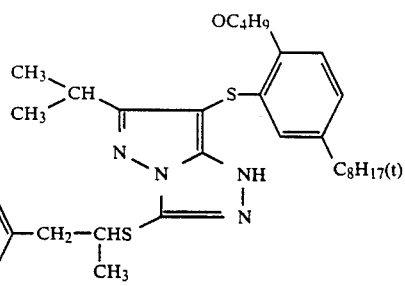 (M-33)

-continued
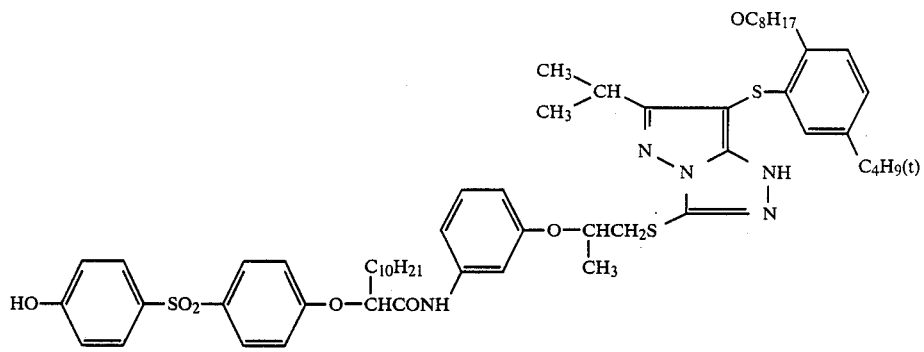 (M-34)
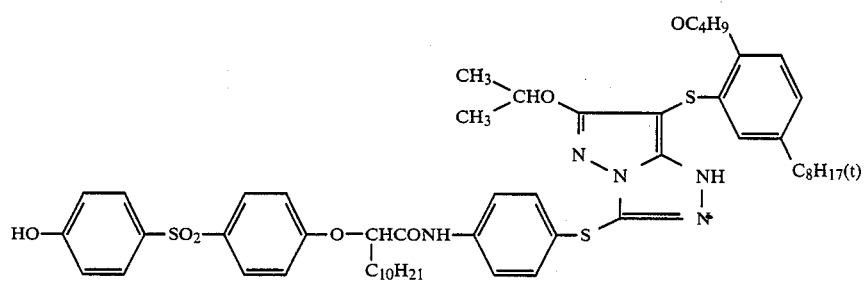 (M-35)
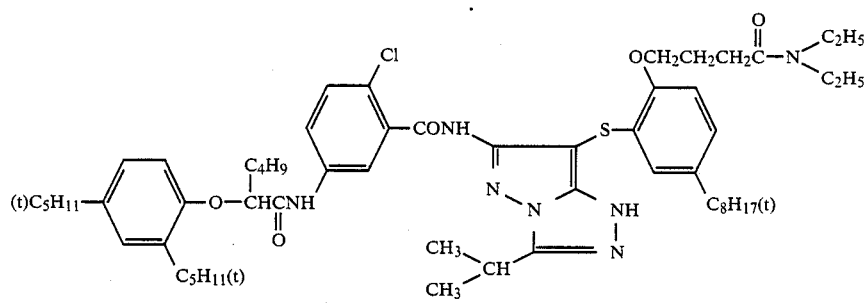 (M-36)
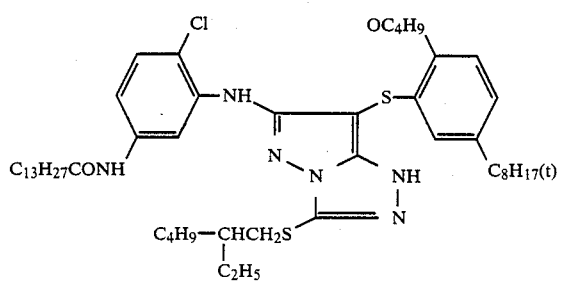 (M-37)
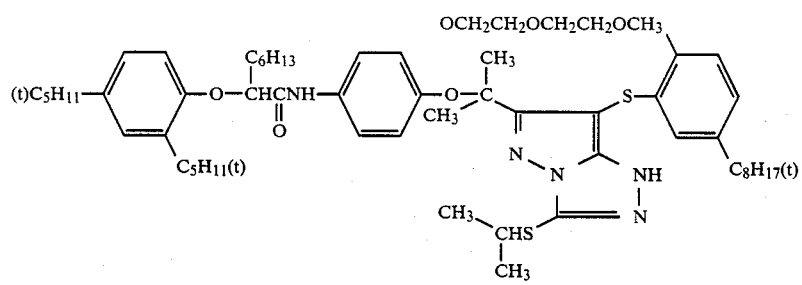 (M-38)

-continued

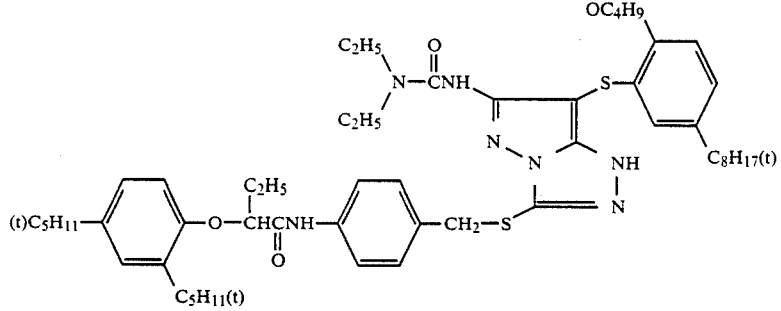
(M-39)

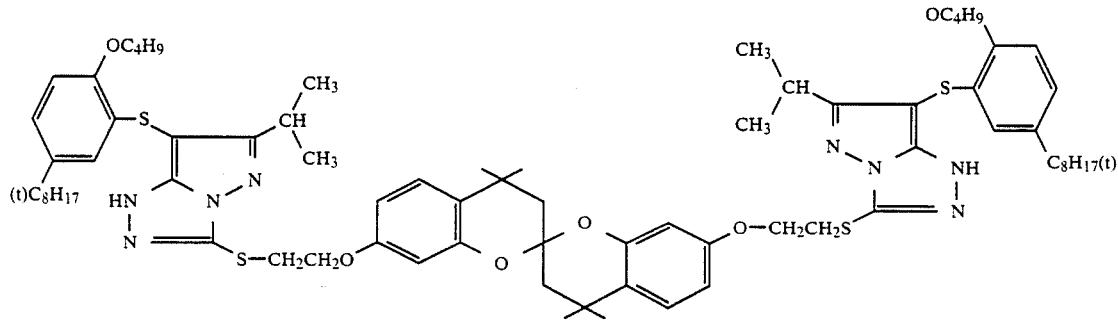
(M-40)

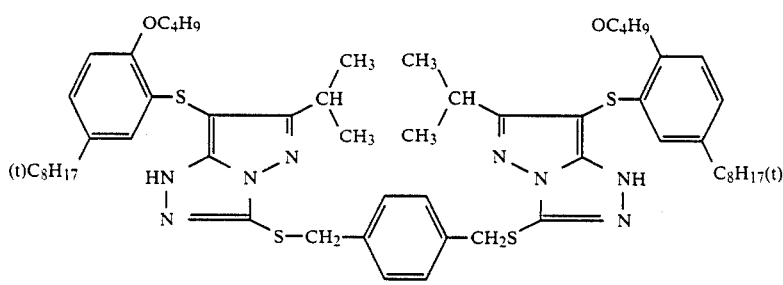
(M-41)

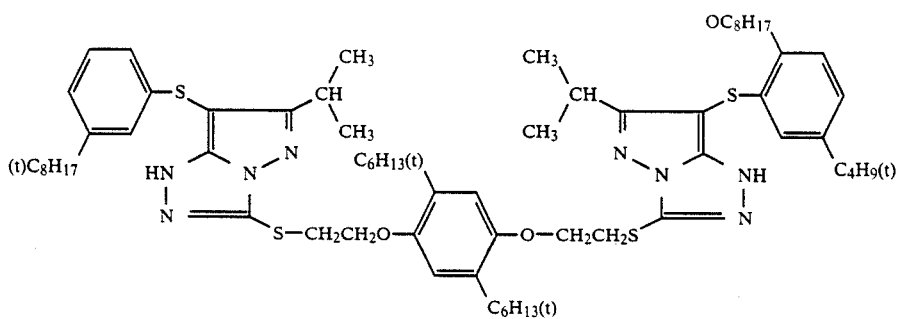
(M-42)

General synthesis methods for the magenta couplers for use in this invention are explained below.

First, methods for producing pyrazoloazole couplers having no substituent at the coupling active site are described. That is, a 1H-pyrazolo[1,5-b]-1,2,4-triazole nucleus can be synthesized by the method described in Japanese Patent Application (OPI) No. 171956/84, a 1H-pyrazolo[3,2-c]-1,2,4-triazole nucleus can be synthesized by the method described in U.S. Pat. 3,725,067, a 1H-imidazo[1,2-b]pyrazole nucleus can be synthesized by the method described in Japanese Patent Application (OPI) No. 162548/84, and a 1H-pyrazolo[1,5-d]tetrazole nucleus can be produced by the method described in Japanese Patent Application (OPI) No. 33552/85.

Into the pyrazoloazole couplers having no substituent at the coupling active site produced by the aforesaid methods, a mercapto split-off group can be introduced by the following method.

That is, the pyrazoloazole coupler having an aromatic mercapto group or a heterocyclic mercapto group at the 7-position thereof as a substituent can be synthesized by the method described in U.S. Pat. No. 4,351,897. Particularly, the coupler can be synthesized by dissolving an aryl mercaptan, a heterocyclic mercaptan, or a corresponding disulfide thereto in a halogenated hydrocarbon solvent, etc., forming a corresponding sulfenyl chloride by chlorine or sulfuryl chloride, and adding thereto a four-equivalent coupler dissolved in an aprotic solvent. Also, the pyrazoloazole coupler having an alkylmercapto group at the 7-position thereof can be synthesized by the method described in U.S. Pat.

No. 4,264,723. That is, the method of introducing a mercapto group to the coupling active site of the coupler and then acting a halide to the mercapto group and the method of synthesizing the coupler in one step by an S-(alkylthio)isothiourea and a hydrochloric acid salt or a hydrobromic acid salt are effective.

Then, some examples of the synthesis methods for the magenta couplers for use in this invention are illustrated below.

Synthesis Example 1: Synthesis of Coupler (M-1)

To 40 ml of a dimethylformamide solution of 16.1 g (0.0189 mole) of 6-ethoxy-2-{2-[2-p-methoxyphenoxy-5-(2-octyloxy-5-tert-octylphenylsulfonamido)phenylsulfonamido]ethyl}-H-pyrazolo[1,5-b]-1,2,4-triazole was added 2-butoxy-5-tert-octylsulfenyl chloride (a methylene chloride solution the volume of which was reduced to 10 ml under reduced pressure after reaction) prepared by previously dissolving 5.6 g (0.0095 mole) of 2-butoxy-5-tert-octyl disulfide in 20 ml of methylene chloride and adding thereto 1.3 g (0.0095 mole) of sulfuryl chloride at room temperature, and after stirring the mixture for one hour at 42° to 45° C., the reaction mixture was extracted with ethyl acetate and then dried. The extract was concentrated and purified by silica gel column chromatography to provide 17.8 g of Coupler (M-1) having a melting point of 103° C. to 107° C.

Mass Analysis (FD): 1144 (M+).
Elemental Analysis:

|  | C | H | N |
|---|---|---|---|
| Calculated: | 63.93% | 7.74% | 7.34% |
| Found: | 63.98% | 7.72% | 7.28% |

Synthesis Example 2: Synthesis of Coupler (M-26)

In 20 ml of dimethylformamide was dissolved 3.7 g of 3-methylthio-6-isopropyl-1H-pyrazolo[5,1-c]-1,2,4-triazole (melting point: 127° C. to 128° C.), and after adding thereto 2-butoxy-5-tert-octylsulfenyl chloride (synthesized using 5.6 g of 2-butoxy-5-tert-octyl disulfide and 1.3 g of sulfuryl chloride) prepared by the method described above in Synthesis Example 1, the mixture was stirred for one hour at 40° C. to 50° C. The reaction mixture thus obtained was extracted with ethyl acetate, and the extract was concentrated and purified by silica gel column chromatography to provide 7.6 g of pale-yellow oil Coupler (M-26).

Mass Analysis (FD): 488 (M+).
Elemental Analysis:

|  | C | H | N |
|---|---|---|---|
| Calculated: | 63.88% | 8.25% | 11.47% |
| Found: | 63.92% | 8.23% | 11.50% |

It will be easily understood that other magenta couplers for use in this invention can be also synthesized in a similar manner to the above.

Couplers other than magenta coloring couplers (viz., cyan couplers and yellow couplers) for use in this invention can be represented by formulae (V) to (VII) below.

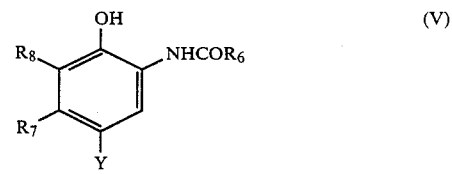 (V)

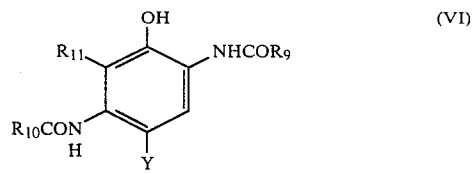 (VI)

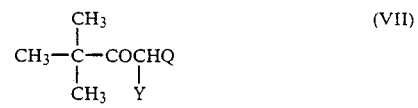 (VII)

In the above formulae, $R_6$, $R_9$, and $R_{10}$ each represents an aliphatic group, an aromatic group, a heterocyclic group, an aromatic amino group, or a heterocyclic amino group; $R_7$ represents an aliphatic group; $R_8$ and $R_{11}$ each represents a hydrogen atom, a halogen atom, an aliphatic group, an aliphatic oxy group, or an acylamino group; Y represents a split-off group; and Q represents a substituted or unsubstituted N-phenylcarbamoyl group.

In formulae (V) and (VI), said $R_7$ and $R_8$ or said $R_{10}$ and $R_{11}$ may be taken together to form a 5-, 6-, or 7-membered ring. Furthermore, each of the couplers shown by formulae (V) to (VII) may form a dimer or more oligomer or polymer at $R_6$, $R_7$, $R_8$, $R_9$, $R_{10}$, $R_{11}$, Y, or Q.

The aliphatic group described above means a straight chain, branched, or cyclic alkyl, alkenyl, or alkynyl group.

Then, specific examples of the cyan couplers and yellow couplers shown by formulae (V), (VI), and (VII) described above are illustrated below, but the invention is not limited to these compounds.

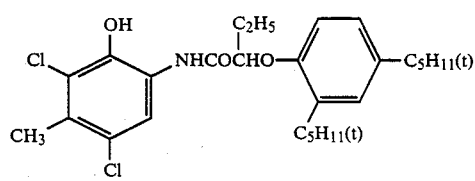 (V-1)

-continued
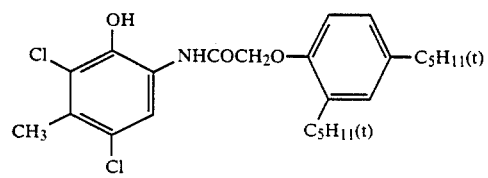 (V-2)
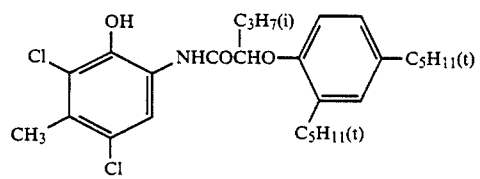 (V-3)
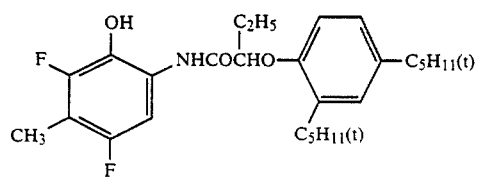 (V-4)
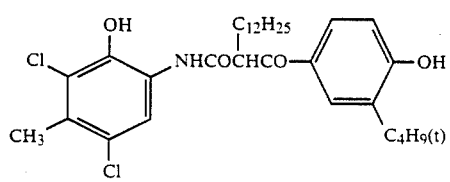 (V-5)
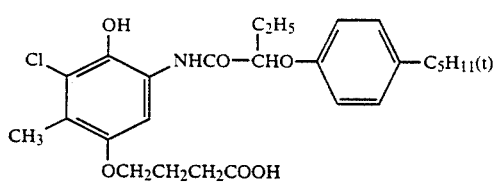 (V-6)
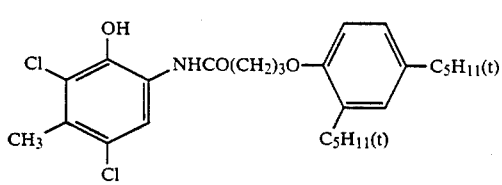 (V-7)
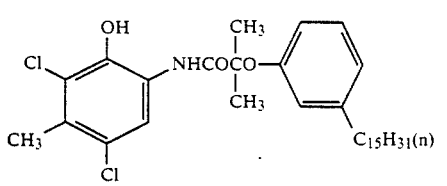 (V-8)
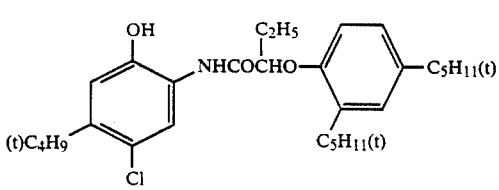 (V-9)

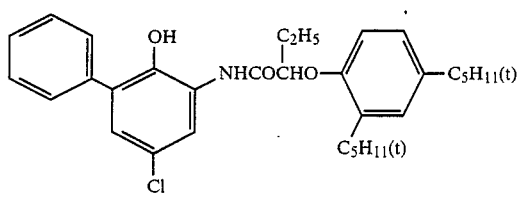 (V-10)
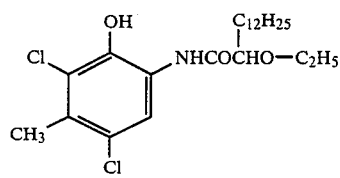 (V-11)
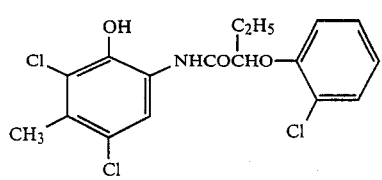 (V-12)
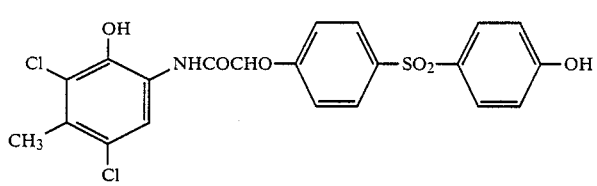 (V-13)
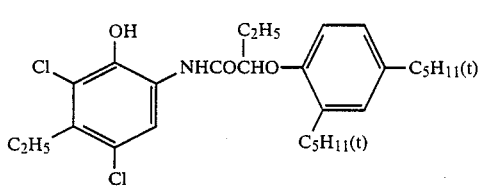 (V-14)
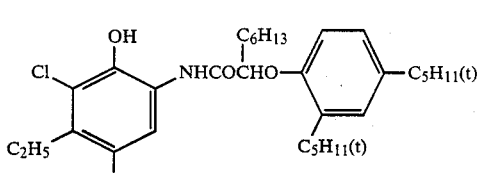 (V-15)
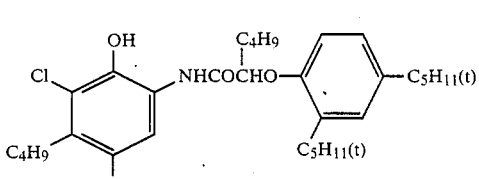 (V-16)
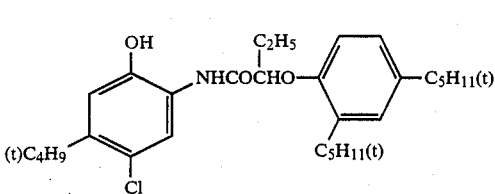 (V-17)

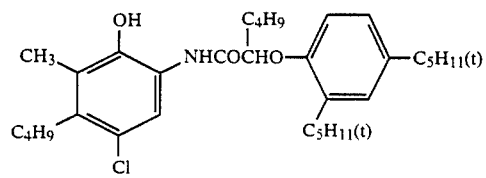 (V-18)
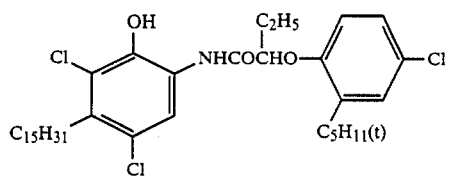 (V-19)
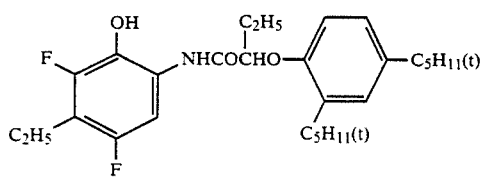 (V-20)
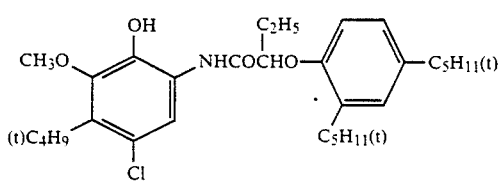 (V-21)
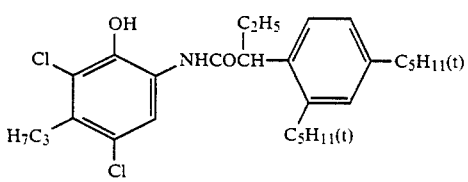 (V-22)
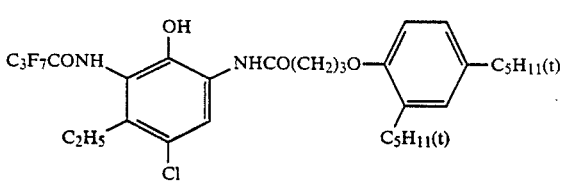 (V-23)
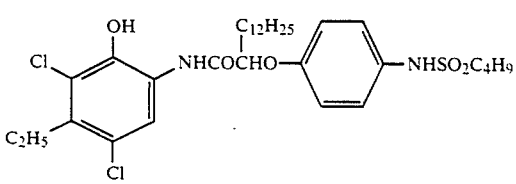 (V-24)
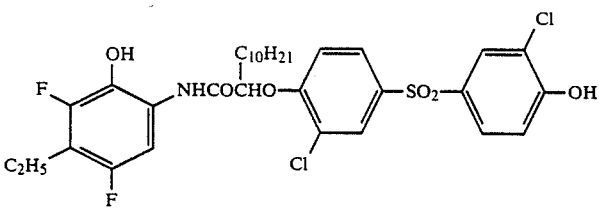 (V-25)

-continued

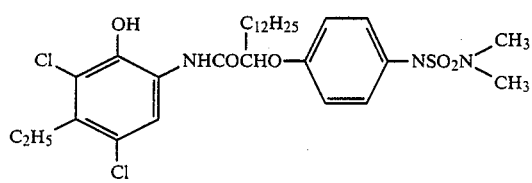
(V-26)

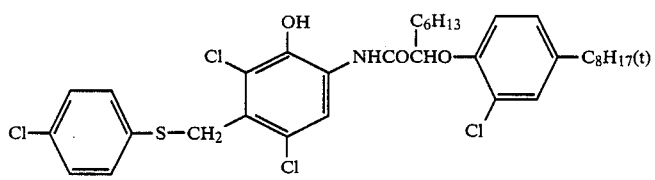
(V-27)

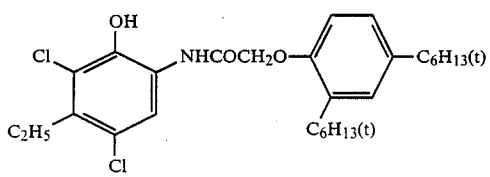
(V-28)

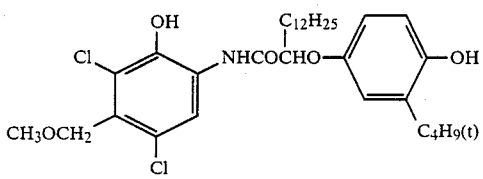
(V-29)

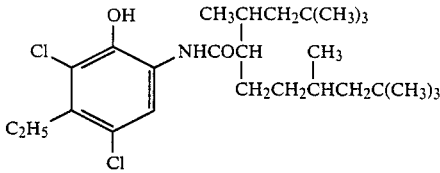
(V-30)

Each of the couplers represented by formulae (I), (V), (VI), and (VII) described above is incorporated in a silver halide emulsion layer constituting a color photographic material in an amount of usually from 0.1 to 1.0 mole, preferably from 0.1 to 0.5 mole, per mole of silver halide in the emulsion layer.

Also, the molar ratio of the magenta coupler, the cyan coupler, and the yellow coupler shown by formula (I), formula (V) or (VI), and formula (VII), respectively, is about 1/0.2–1.5/0.5–1.5, but other ranges can be employed.

For incorporating the aforesaid couplers in silver halide emulsion layer, various techniques can be employed. Ordinarily, an oil drop-in-water dispersion method known as the oil-protective method can be employed for dispersing the coupler in a silver halide emulsion, and, in this case, the use of a high-boiling organic solvent represented by formulae (A), (B), (C), (D), or (E) shown below is preferred. Also, the aforesaid organic solvent having a dielectric constant of at least 4.00 (25° C., 10 KHz) is particularly preferred.

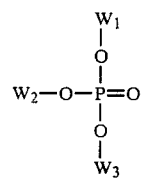
(A)

(B)

$W_1-COO-W_2$

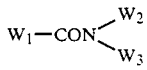
(C)

$W_1-CON{\overset{W_2}{\underset{W_3}{}}}$

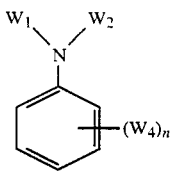
(D)

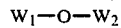
(E)

$W_1-O-W_2$

In the above formulae, $W_1$, $W_2$, and $W_3$ each represents a substituted or unsubstituted alkyl group, a substituted or unsubstituted cycloalkyl group, a substituted or unsubstituted alkenyl group, a substituted or unsubstituted aryl group, or a substituted or unsubstituted heterocyclic group; $W_4$ represents $W_1$, $O-W_1$, or $S-W_2$; and n represents an integer of from 1 to 5; when n is 2 or more, said $R_4$ groups may be the same or different, and in formula (E), $W_1$ and $W_2$ may form a condensed ring.

Specific but nonlimitative examples of the high-boiling organic solvents represented by formulae (A) to (E) are shown below:

$$O=P(OC_4H_9-\underline{n})_3 \quad \text{(S-1)}$$

$$O=P(OCH_2CH_2CHCH_3)_3 \quad \text{(S-2)}$$
$$\phantom{O=P(OCH_2CH_2C}|\phantom{CH_3)_3}$$
$$\phantom{O=P(OCH_2CH_2}CH_3$$

$$O=P(OC_6H_{13}-\underline{n})_3 \quad \text{(S-3)}$$

(S-4) $O=P{\left(O-\text{cyclopentyl}\right)}$ (S-5) $O=P{\left(O-\text{cyclohexyl}\right)}$ $$O=P(OC_8H_{17}-\underline{n})_3 \quad \text{(S-6)}$$

$$O=P\left(OCH_2CHC_4H_9-\underline{n}\atop CH_2CH_3\right)_3 \quad \text{(S-7)}$$

$$O=P\left(OCH_2\underset{CH_3}{\overset{CH_3}{C}}CH_2CHCH_3\atop CH_3\right)_3 \quad \text{(S-8)}$$

$$O=P\left(O-(CH_2)_6\overset{CH_3}{\underset{}{C}}HCH_3\right)_3 \quad \text{(S-9)}$$

$$O=P(OC_9H_{19}-\underline{n})_3 \quad \text{(S-10)}$$

$$O=P\left(OCH(CH_2)_6CH_3\atop CH_3\right)_3 \quad \text{(S-11)}$$

$$O=P(OC_{10}H_{21}-\underline{n})_3 \quad \text{(S-12)}$$

$$O=P\left(OCH_2CH_2CHCH_2CH_2\overset{CH_3}{\underset{CH_3}{C}}CH_3\atop CH_3\right)_3 \quad \text{(S-13)}$$

$$O=P\overset{O(CH_2)_6CH(CH_3)_2}{\underset{[O(CH_2)_7CH(CH_3)_2]_2}{}} \quad \text{(S-14)}$$

$$O=P\overset{OC_4H_9-\underline{n}}{\underset{(OC_{12}H_{25}-\underline{n})_2}{}} \quad \text{(S-15)}$$

-continued (S-16) $O=P{\left(O-\text{C}_6\text{H}_4-CH_3\right)_3}$ (S-17) $O=P{\left(O-\text{C}_6\text{H}_4-OC_4H_9-\underline{n}\right)_3}$ (S-18) $O=P{\left(O-\text{C}_6\text{H}_4-F\right)_3}$ (S-19) $O=P{\left(O-\text{C}_6\text{H}_4-CH_3\right)_2}$
$$\phantom{O=P}OCH_2CHC_4H_9-\underline{n}$$
$$\phantom{O=POCH_2CH}|$$
$$\phantom{O=POCH_2}C_2H_5$$

$$O=P\left[O(CH_2)_5CH-CH_2\atop\underset{O}{\smile}\right]_3 \quad \text{(S-20)}$$

$$O=P\left[O(CH_2)_7CH-CH_2\atop\underset{O}{\smile}\right]_3 \quad \text{(S-21)}$$

$$O=P\left[OCH_2\overset{C_2H_5}{\underset{}{C}}HC_4H_9\right]_2 \quad \text{(S-22)}$$
$$\phantom{O=P}OCH_2CH_2CH-CH_2$$
$$\phantom{O=POCH_2CH_2CH}\underset{O}{\smile}$$

(S-23) benzene-1,2-di(COOCH$_3$)

(S-24) benzene-1,2-di(COOC$_3$H$_7$(n))

(S-25) benzene-1,2-di(COOC$_4$H$_9$(n))

(S-26) benzene-1,2-di(COOC$_4$H$_9$(iso))

(S-27) benzene-1,2-di(COOC$_5$H$_{11}$(n))

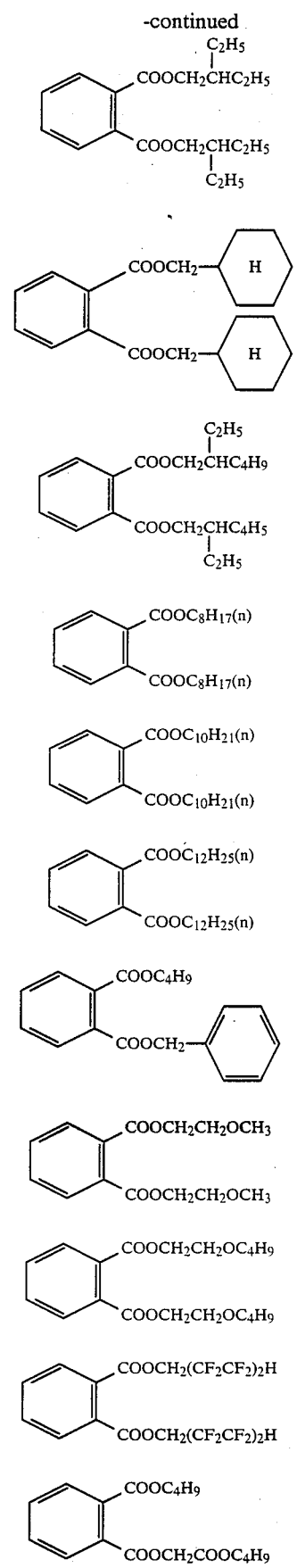
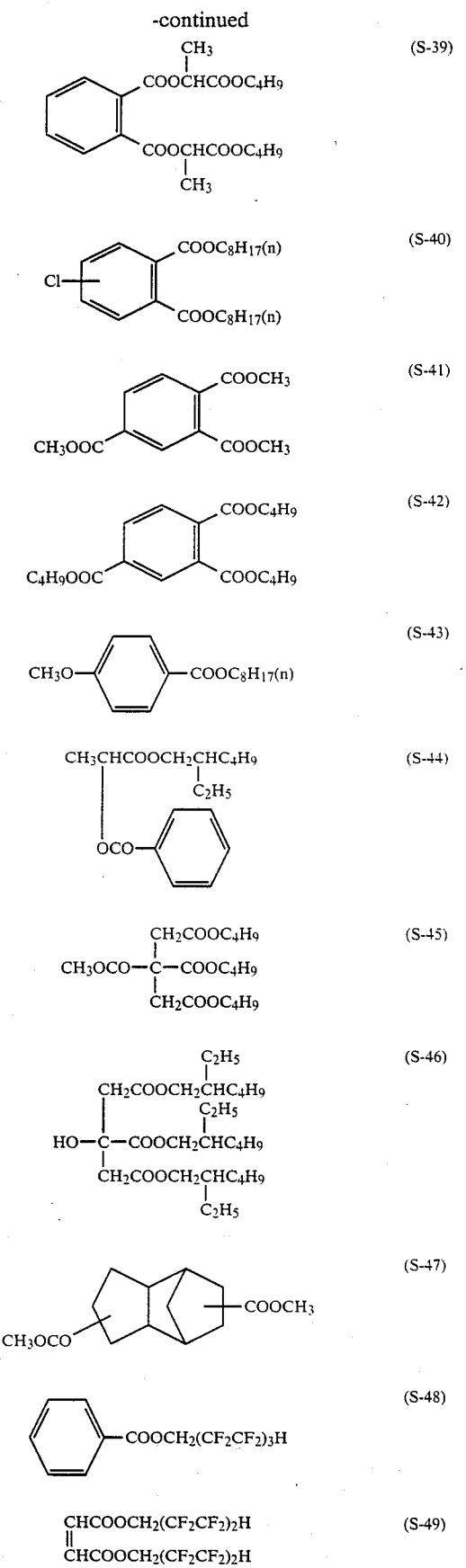

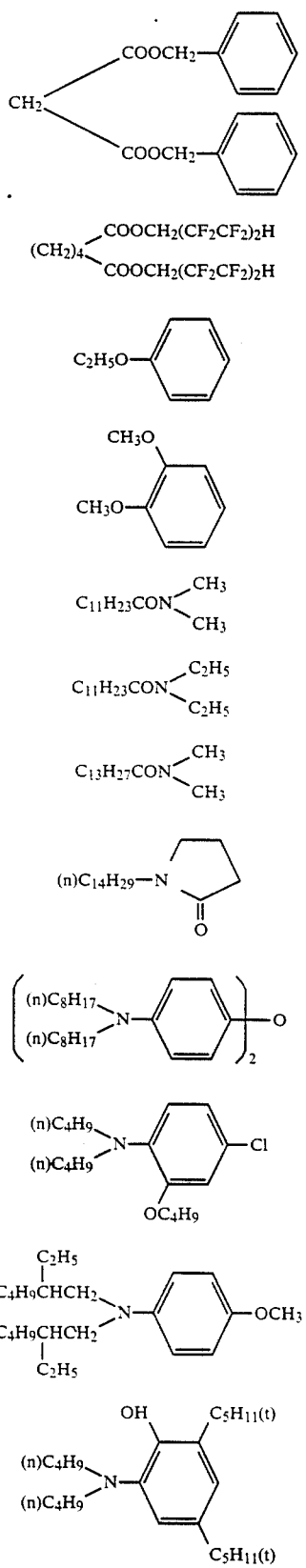

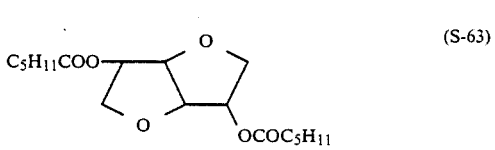
(S-63)

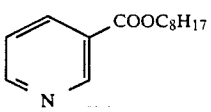
(S-64)

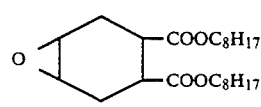
(S-65)

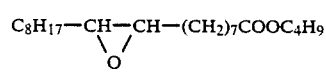
(S-66)

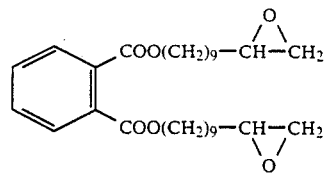
(S-67)

The light-sensitive materials of the invention can contain an ultraviolet absorbent in any optional layer. The ultraviolet absorbent is preferably incorporated in a layer containing the compound represented by formula (V) or (VI) or a layer adjacent thereto.

Examples of the ultraviolet absorbents which can be used in the present invention are recited in Research Disclosure, RD No. 17643, VIII-C. Preferred among them are benzotriazole derivatives represented by formula (VIII)

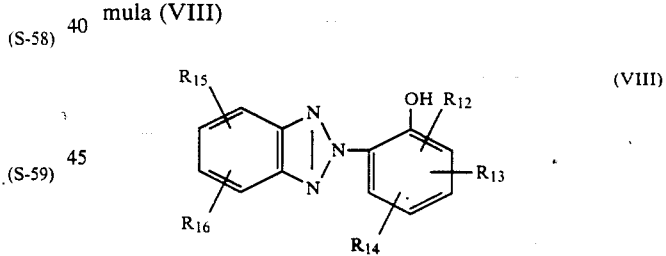
(VIII)

wherein $R_{12}$, $R_{13}$, $R_{14}$, $R_{15}$, and $R_{16}$ (which may be the same or different) each represents a hydrogen atom or a substituent; and $R_{15}$ and $R_{16}$ may be cyclized to form a 5- or 6-membered carbon ring. The substituent as represented by $R_{12}$, $R_{13}$, $R_{14}$, $R_{15}$, or $R_{16}$ is selected from those enumerated for the groups as represented by $R_1$ or $R_1'$. Of these groups, those which may have any substituent may be substituted with the substituents described for $R_1$ or $R_1'$.

The compounds represented by formula (VIII) can be used either individually or in combinations of two or more thereof. Typical examples of these compounds are shown below:

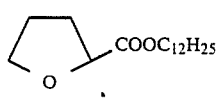

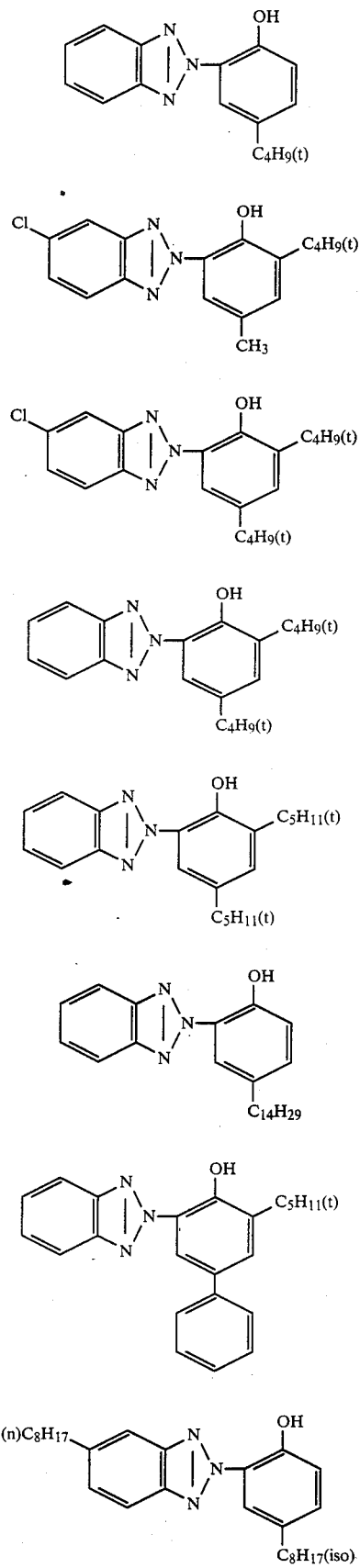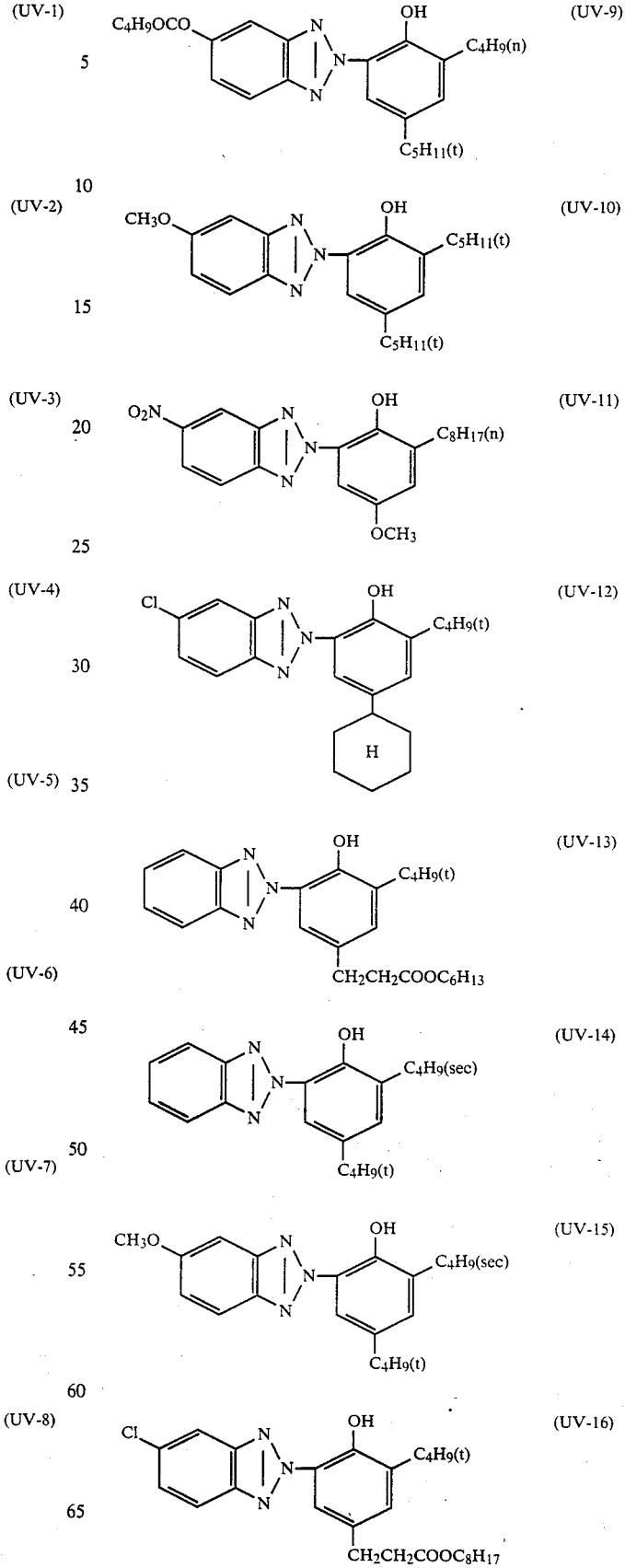

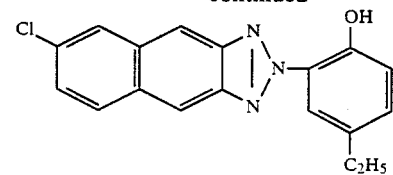 (UV-17)

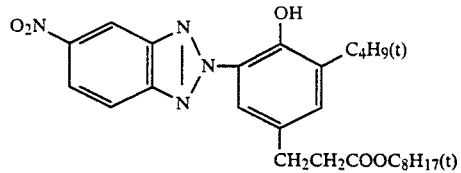 (UV-18)

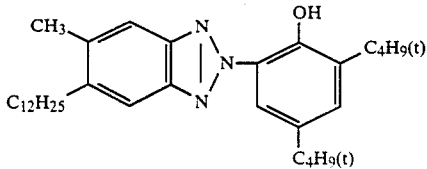 (UV-19)

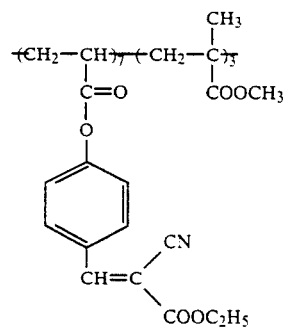 (UV-20)

In order to further improve preservability of developed dye images, i.e., yellow, cyan, and magenta dye images, various organic type and metal complex type discoloration inhibitors can be used. The organic discoloration inhibitors include hydroquinones, gallic acid derivatives, p-alkoxyphenols, p-hydroxyphenols, etc. Examples of dye image stabilizers, stain inhibitors, or antioxidants are described in patents cited in *Research Disclosure*, RD No. 17643, VII-I to J. Examples of the metal complex type discoloration inhibitors are described in *Research Disclosure*, RD. No. 15162, etc.

Heat- and light-fastness of yellow images can be improved by using a number of compounds belonging to phenols, hydroquinones, hydroxychromans, hydroxycoumarans, and hindered amines, and alkyl ethers, silyl ethers or hydrolyzable precursors thereof. Of these compounds, those represented by formulae (IX) and (X) shown below are particularly effective to improve fastness of cyan images and yellow images to both light and heat. These compounds are effective to improve fastness of cyan images also.

Formula (IX) is represented by

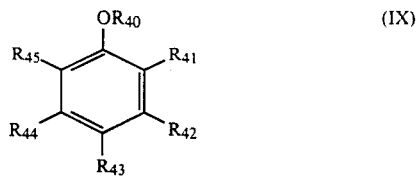 (IX)

wherein $R_{40}$ represents a hydrogen atom, a substituted or unsubstituted aliphatic group, a substituted or unsubstituted aromatic group, a substituted or unsubstituted heterocyclic group, or a substituted silyl group of formula $$-Si\begin{pmatrix}R_{50}\\R_{51}\\R_{52}\end{pmatrix},$$

wherein $R_{50}$, $R_{51}$, and $R_{52}$ (which may be the same or different) each represents a substituted or unsubstituted aliphatic group, a substituted or unsubstituted aromatic group, a substituted or unsubstituted aliphatic oxy group, or a substituted or unsubstituted aromatic oxy group, wherein the substituent is selected from those acceptable for $R_1$ or $R_1'$; and $R_{41}$, $R_{42}$, $R_{43}$, $R_{44}$ and $R_{45}$ (which may be the same or different) each represents a hydrogen atom, an alkyl group, an aryl group, an alkoxy group, a hydroxyl group, an alkoxycarbonyl group, a mono- or dialkylamino group, an imino group, or an acylamino group.

Formula (X) is represented by

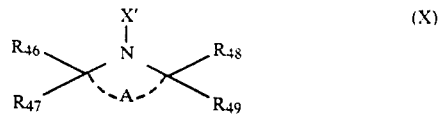 (X)

wherein $R_{46}$, $R_{47}$, $R_{48}$, and $R_{49}$ (which may be the same or different) each represents a hydrogen atom or an alkyl group; X' represents a hydrogen atom, an aliphatic group, an acyl group, an aliphatic or aromatic sulfonyl group, an aliphatic or aromatic sulfinyl group, an oxy radical group, or a hydroxyl group; and A represents a non-metallic atomic group forming a 5-, 6-, or 7-membered ring.

Specific but nonlimitative examples of the compounds of formula (IX) or (X) are shown below:

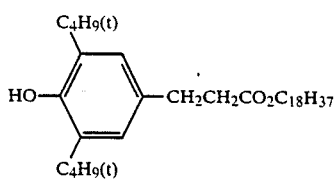 B-1

-continued
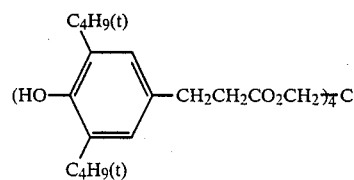 B-2
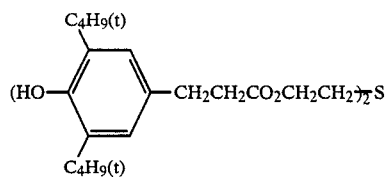 B-3
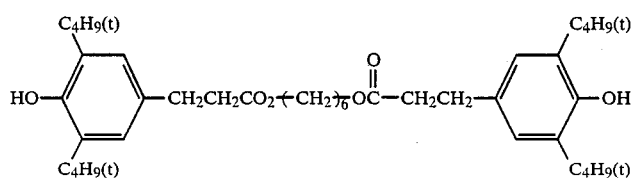 B-4
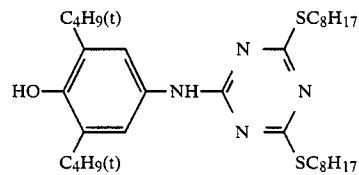 B-5
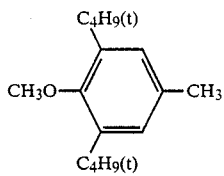 B-6
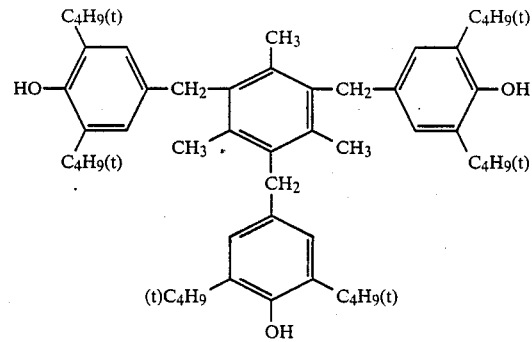 B-7
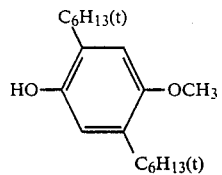 B-8
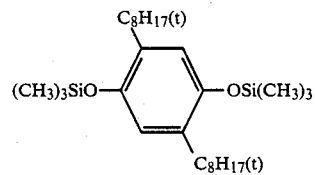 B-9

-continued
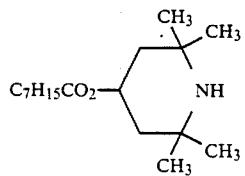 B-10
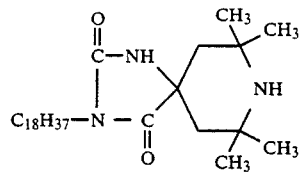 B-11
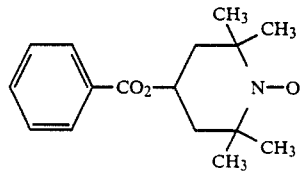 B-12
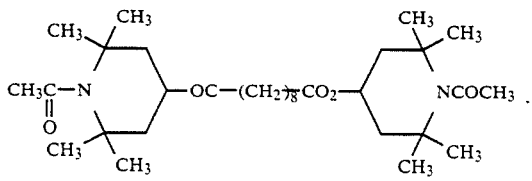 B-13
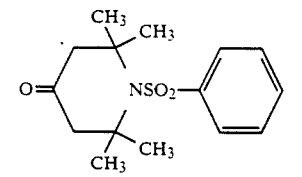 B-14
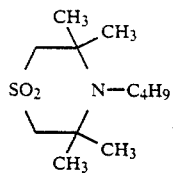 B-15
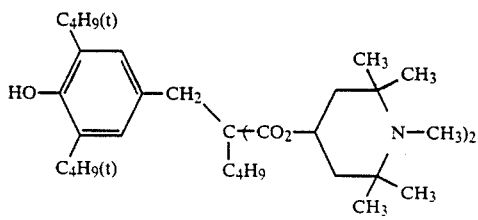 B-16
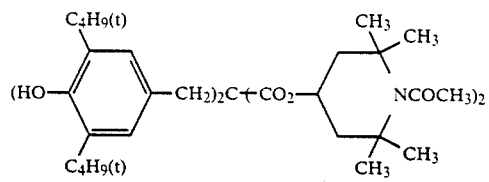 B-17
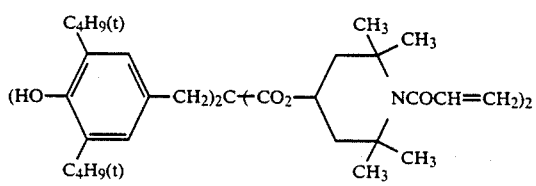 B-18

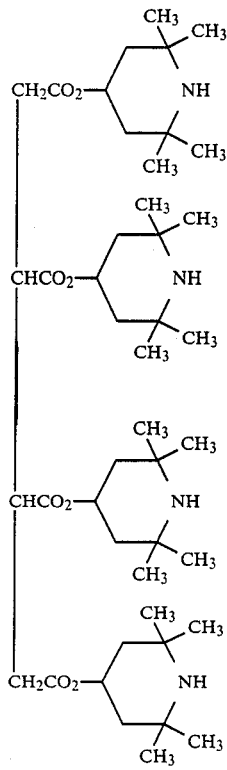

B-19

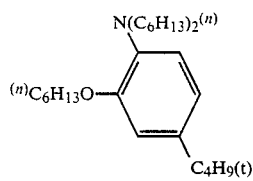

B-20

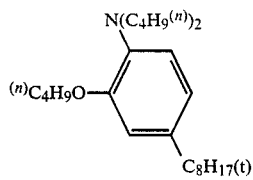

B-21

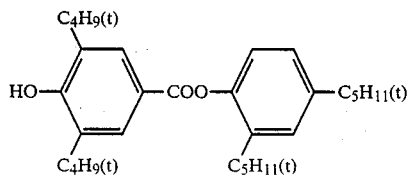

B-22

The compounds of formulae (IX) and (X) may be used individually or in combinations of two or more thereof or in combinations with other conventionaly known discoloration inhibitors.

While the aforesaid dye image stabilizers, stain inhibitors and antioxidants are also effective to improve preservability of the magenta dye obtained from the coupler of formula (I), compounds represented by formulae (XI), (XII), (XIII), (XIV), (XV), and (XVI) shown below are particularly preferred for their effect to improve the fastness to light.

Formula (XI) is represented by

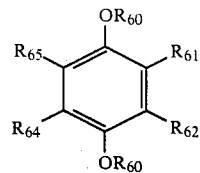

(XI)

wherein $R_{60}$ has the same meaning as $R_{40}$ in formula (IX); and $R_{61}$, $R_{62}$, $R_{64}$, and $R_{65}$ (which may be the same or different) each represents a hydrogen atom, an aliphatic group, an aromatic group, an acylamino group, a mono- or dialkylamino group, an aliphatic or aromatic thio group, an aliphatic or aromatic oxycarbonyl group, or —$OR_{60}$; $R_{60}$ and $R_{61}$ may be bonded together to form a 5- or 6-membered ring; and $R_{61}$ and $R_{62}$ may be bonded together to form a 5- or 6-membered ring.

Formula (XII) is represented by

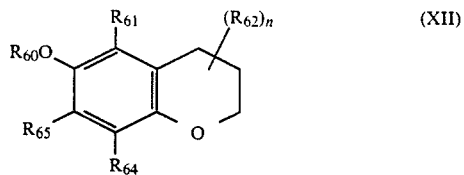

wherein $R_{60}$, $R_{61}$, $R_{62}$, $R_{64}$, and $R_{65}$ are as defined above; and n represents 0 or an integer or from 1 to 6.

Formula (XIII) is represented by

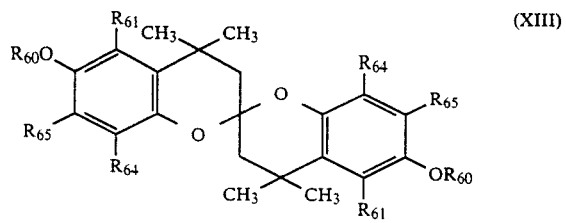

wherein $R_{60}$, $R_{61}$, $R_{64}$, and $R_{65}$ are as defined above.

Formula (XIV) is represented by

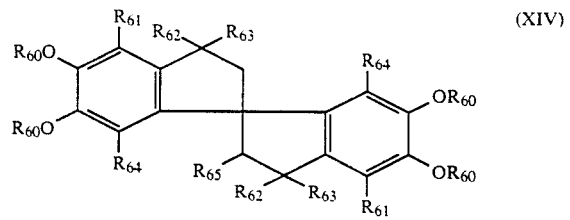

wherein $R_{60}$, $R_{61}$, $R_{62}$, $R_{64}$, and $R_{65}$ are as defined above; and $R_{63}$ has the same meaning as $R_{60}$ to $R_{65}$.

Formula (XV) is represented by

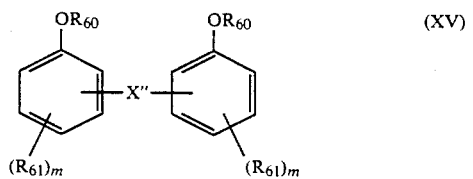

wherein $R_{60}$ and $R_{61}$ are as defined above; X″ represents a divalent linking group; and m represents 0 or a integer of from 1 to 4.

Formula (XVI) is represented by

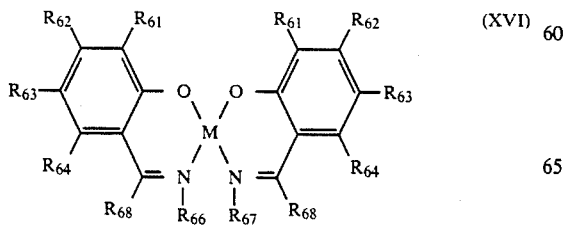

wherein $R_{61}$, $R_{62}$, $R_{63}$, and $R_{64}$ are as defined above; $R_{66}$ and $R_{67}$ (which may be the same or different) each represents a hydrogen atom, an aliphatic group, an aromatic group, or a hydroxyl group; $R_{68}$ represents a hydrogen atom, an aliphatic group, or an aromatic group; $R_{66}$ and $R_{67}$ may be taken together to form a 5- or 6-membered ring; and M represents Cu, Co, Ni, Pd, or Pt.

In formulae (XI) to (XVI), the aliphatic group or aromatic group as represented by $R_{61}$, $R_{62}$, $R_{63}$, $R_{64}$, $R_{65}$, $R_{66}$, $R_{67}$, or $R_{68}$ may be substituted with the substituents acceptable for $R_1$ or $R_1'$. When n or m is 2 or more, two or more groups $R_{62}$ or $R_{61}$ may be the same or different.

In formula (XV), typical example of X″ preferably include

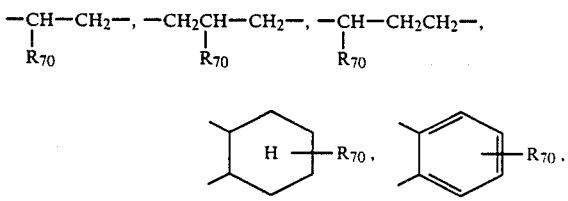

etc., wherein $R_{70}$ represents a hydrogen atom or an alkyl group. $R_{61}$ in formula (XVI) preferably represents a group capable of forming a hydrogen bond. At least one of $R_{62}$, $R_{63}$, and $R_{64}$ is preferably a hydrogen atom, a hydroxyl group, an alkyl group, or an alkoxy group. A total number of carbon atoms contained in $R_{61}$, $R_{62}$, $R_{63}$, $R_{64}$, $R_{65}$, $R_{66}$, $R_{67}$, and $R_{68}$ is preferably 4 or more.

Specific but non-limitative examples of the compounds represented by formulae (XI) to (XVI) are shown below:

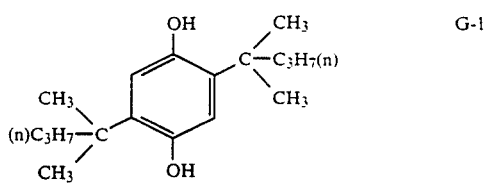

G-1

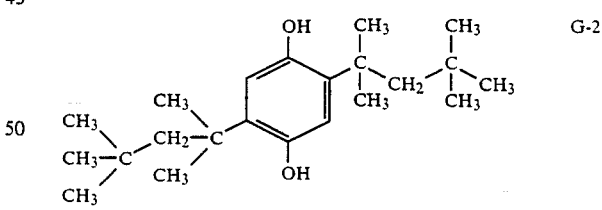

G-2

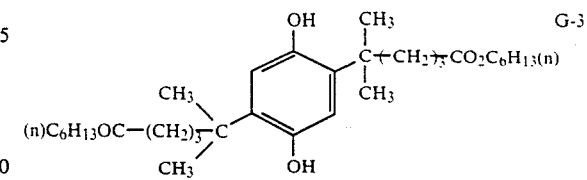

G-3

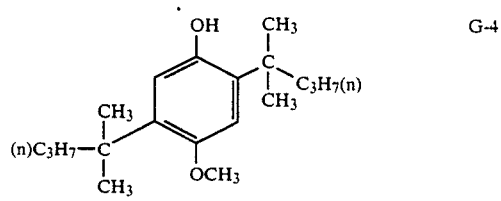

G-4

-continued
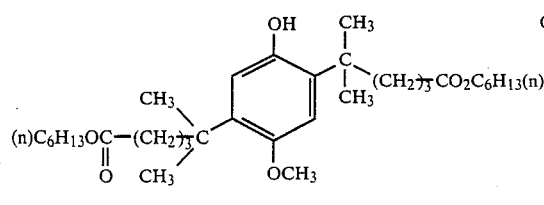 G-5
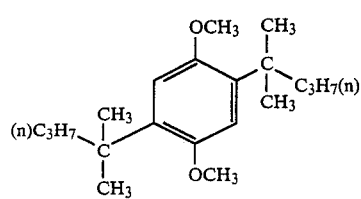 G-6
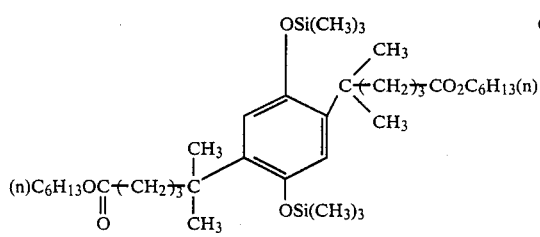 G-7
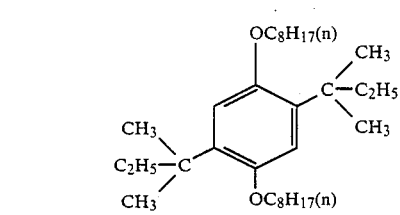 G-8
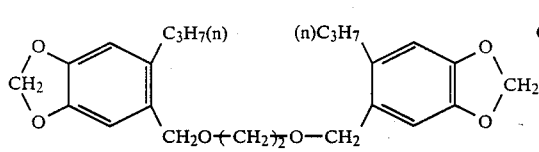 G-9
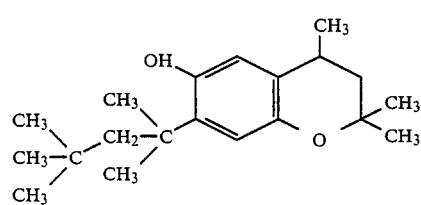 G-10
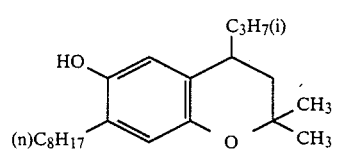 G-11
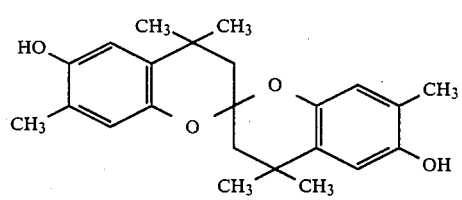 G-12
-continued
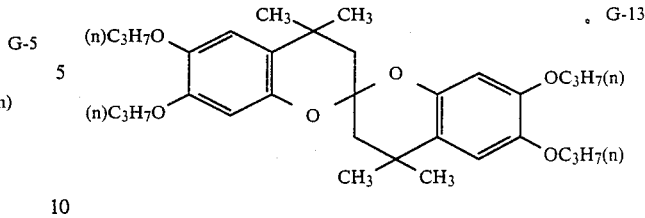 G-13
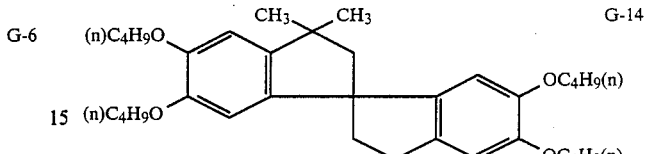 G-14
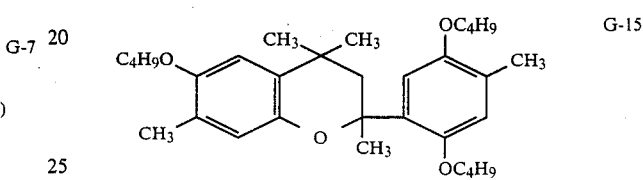 G-15
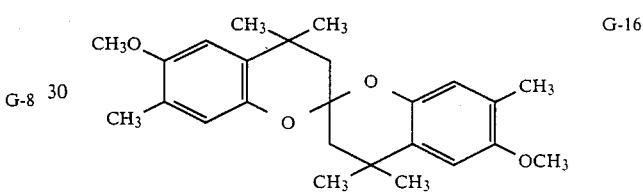 G-16
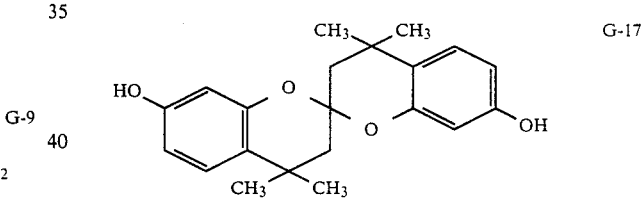 G-17
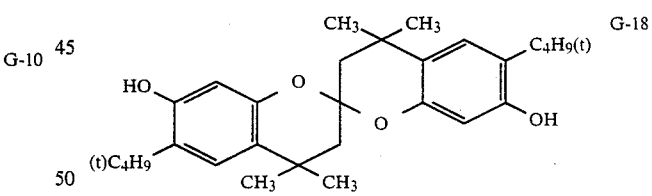 G-18
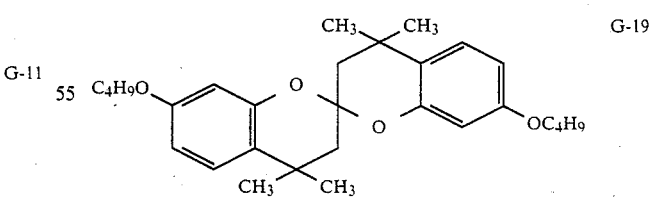 G-19
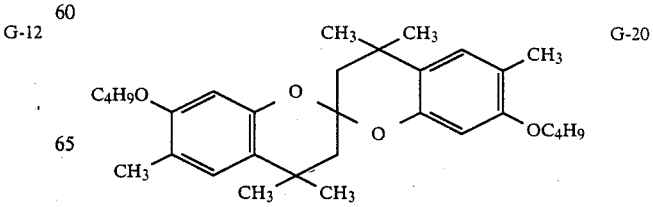 G-20

-continued

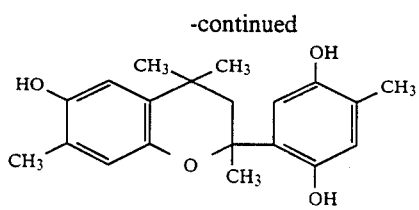

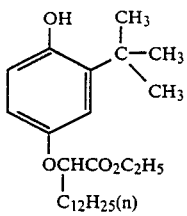

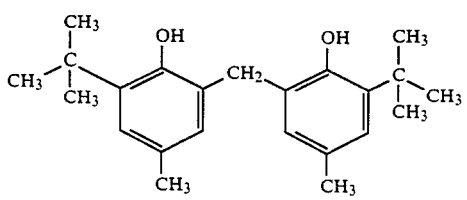

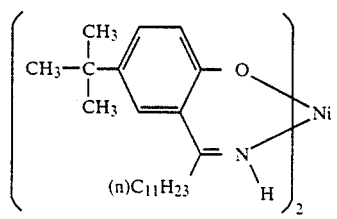

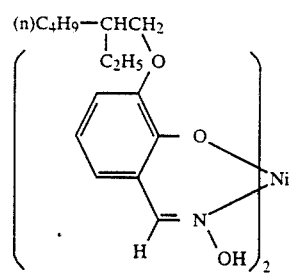

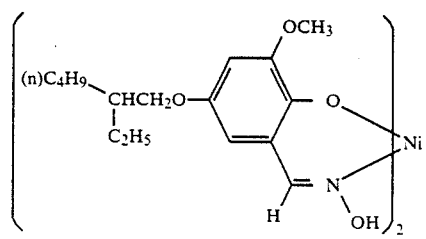

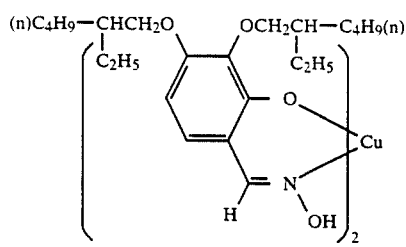

-continued

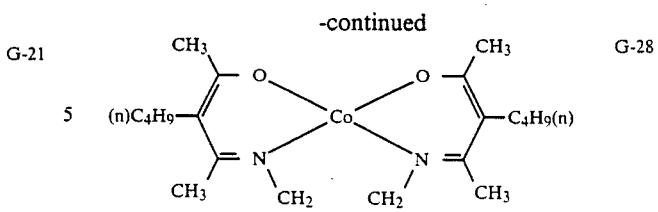

G-21

G-22

G-23

G-24

G-25

G-26

G-27

G-28

G-29

As the support which can be used in the present invention, any of transparent supports such as polyethylene terephthalate and cellulose triacetate and reflective supports can be used, with reflective supports being preferred.

A reflective support which can be used in the present invention is a support which has heightened reflecting properties to make a dye image formed in a silver halide emulsion layer cleaner. Such a reflective support includes a support having coated thereon a hydrophobic resin having dispersed therein a light reflecting substance, e.g., titanium oxide, zinc oxide, calcium carbonate, calcium sulfate, etc., and a support made of such a light reflecting substance-containing hydrophobic resin per se. Examples of the reflective support are baryta paper, polyethylene-coated paper, polypropylene-based synthetic paper, and transparent supports having a reflective layer or containing a reflective substance, such as a glass sheet, polyester films, e.g., polyethylene terephthalate, cellulose triacetate, cellulose nitrate, etc., polyamide films, polycarbonate films, polystyrene films, and the like. The support to be used can be selected appropriately from among them according to the end use.

The blue-sensitive, green-sensitive, or red-sensitive emulsion according to the present invention is obtained by spectrally sensitizing the respective layer with methine dyes or others so as to have the respective color sensitivity. Sensitizing dyes to be used include cyanine dyes, merocyanine dyes, complex cyanine dyes, complex merocyanine dyes, holopolar cyanine dyes, hemicyanine dyes, styryl dyes, and hemioxonol dyes. Particularly preferred are cyanine dyes, merocyanine dyes, and complex merocyanine dyes. Any of nuclei commonly utilized in cyanine dyes as a basic heterocyclic nucleus is applicable to these sensitizing dyes. Specific examples of the applicable nuclei include a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc.; the above-described nucleus to which an alicyclic hydrocarbon ring is fused; and the above-described nucleus to which an aromatic hydrocarbon ring is fused, e.g., an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc. These nuclei may have a substituent on their carbon atoms.

To the merocyanine dyes or complex merocyanine dyes is applicable a 5- to 6-membered heterocyclic nucleus having a ketomethylene structure, e.g., a pyrazolin-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc.

These sensitizing dyes may be used either individually or in combinations thereof. Combinations of sensitizing dyes are frequently used for the purpose of supersensitization. Typical examples of such combinations of sensitizing dyes are described in U.S. Pat. Nos. 2,688,545, 2,977,229, 3,397,060, 3,522,052, 3,527,641, 3,617,293, 3,628,964, 3,666,480, 3,672,898, 3,697,428, 3,703,377, 3,769,301, 3,814,609, 3,837,862, and 4,026,707, British Patents 1,344,281 and 1,507,803, Japanese Patent Publication Nos. 4936/68 and 12375/78, and Japanese Patent Application (OPI) Nos. 110618/77 and 109925/77.

The silver halide emulsions may further contain, in combination with the sensitizing dyes, dyes which do not per se have spectral sensitizing activity, or substances which do not substantially absorb visible light, but which do show supersensitizing effects.

The color photographic material which is used in this invention may have auxiliary layers such as a subbing layer, interlayers, protective layer(s), etc., in addition to the above-described silver halide emulsion layers. Also, if necessary, a ultraviolet absorptive layer may be formed between a red-sensitive silver halide emulsion layer and a green-sensitive silver halide emulsion layer. For the ultraviolet absorptive layer, the ultraviolet absorbent(s) described hereinbefore are preferably used, but other known ultraviolet absorbents may be used.

As a binder or protective colloid for silver halide emulsions, gelatin is advantageously used but other hydrophilic colloids may be used.

Examples of these hydrophilic colloids are proteins such as gelatin derivatives, graft polymers of gelatin and other polymers, albumin, casein, etc.; cellulose derivatives such as hydroxyethyl cellulose, carboxymethyl cellulose, cellulose sulfuric acid esters, etc.; saccharose derivatives such as sodium alginate, starch derivatives, etc.; and various synthetic hydrophilic polymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc.

As gelatin, limed gelatin as well as acid-treated gelatin and also enzyme-treated gelatin as described in *Bull. Soc. Phot. Japan*, No. 16, 30 (1966) can be used. Furthermore, hydrolyzed products or enzyme-decomposed products of gelatin can be used.

The color photographic materials for use in this invention may further contain fluorescent brightening agents such as stilbene series, triazine series, oxazole series, and cumarin series whitening agents in the emulsion layers or other hydrophilic colloid layers. The fluorescent brightening agents may be water-soluble or water-insoluble and in the latter case, they are used in the form of a dispersion. Specific examples of the fluorescent brightening agents are described in U.S. Pat. Nos. 2,632,701, 3,269,840 and 3,359,102, British Patents 852,075 and 1,319,763, *Research Disclosure*, Vol. 176, RD No. 17643 (December 1978), page 24, "Brighteners", etc.

When the color photographic materials for use in this invention contain dyes or ultraviolet absorbent(s) in the hydrophilic colloid layers, the ultraviolet absorbents may be mordanted by a cationic polymer, etc., such as the polymers described in British Patent 685,475, U.S. Pat. Nos. 2,675,316, 2,839,401, 2,882,156, 3,048,487, 3,184,309, and 3,445,231, West German Patent Application (OLS) No. 1,914,362, Japanese Patent Application (OPI) Nos. 47624/75 and 71332/75, etc.

The color photographic materials for use in this invention may further contain hydroquinone derivatives, aminophenol derivatives, gallic acid derivatives, ascorbic acid derivatives, etc., as color antifoggants. Specific examples thereof are described in U.S. Pat. Nos. 2,360,290, 2,336,327, 2,403,721, 2,418,613, 2,675,314, 2,701,197, 2,704,713, 2,728,659, 2,732,300, and 2,735,765, Japanese Patent Application (OPI) Nos. 92988/75, 92989/75, 93928/75, 110337/75, and 146235/77, Japanese Patent Publication No. 23813/75, etc.

The color photographic materials which are used in this invention can further contain, if necessary, various known photographic additives, such as stabilizers, antifoggants, surface active agents, couplers (in addition to the above-described couplers in this invention), filter dyes, irradiation preventing dyes, developing agents, etc.

Furthermore, the color photographic materials for use in this invention may further contain a fine grain silver halide emulsion (e.g., a silver chloride, silver bromide, or silver chlorobromide having a means grain size of less than 0.20 $\mu$m) having substantially no light sensitivity in the silver halide emulsion layers or other hydrophilic colloid layers. The addition of the fine grain silver halide emulsion contributes to inhibition of emulsion fogging which the magenta coupler likely causes during the development by mutual action with the silver halide in the blue-sensitive silver halide emulsion layer containing a yellow coupler. That is, though when the formulation of the developing solution alters, the emulsion fogging likely occurs, by the addition of the fine grain emulsion the occurrence of the emulsion fogging can effectively be inhibited even when the formulation of the developing solution alters.

The light-sensitive silver halide emulsion which is preferably used for the color photographic materials for use in this invention contains silver bromide, silver chlorobromide, or silver chloride, each substantially containing no silver iodide, and particularly preferably contains silver chlorobromide containing from 2 to 80 mole% silver chloride. For attaining the object for rapid processing, it is preferred to use, as the silver halide, silver chloride or silver chlorobromide having a silver chloride content of 90 mole% or more and preferably 95 mole% or more.

The processing steps, i.e., image formation process, according to the present invention will be described below.

According to the present invention, the color development processing is completed within a short processing time of 2 minutes and a half, and preferably in a processing time of from 30 to 130 seconds. The processing time herein referred to means a time of from the contact of a light-sensitive material with a color developing solution to the contact with a subsequent bath, and covers, therefore, the time for transfer between baths.

The color developing solution to be used preferably comprises an alkaline aqueous solution containing an aromatic primary amine color developing agent as a main component. The color developing agent includes p-phenylenediamine compounds to advantage, which typically include 3-methyl-4-amino-N,N-diethylaniline, 3-methyl-4-amino-N-ethyl-N-β-hydroxyethylaniline, 3-methyl-4-amino-4-ethyl-N-β-methanesulfonamidoethylaniline, 3-methyl-4-amino-N-ethyl-N-β-methoxyethylaniline, and sulfates, hydrochlorides, phosphates, p-toluenesulfonates, tetraphenylborates or p-(t-octyl)-benzenesulfonates thereof, and the like. Among them, 3-methyl-4-amino-N-ethyl-N-β-hydroxyethylaniline and 3-methyl-4-amino-N-ethyl-N-β-methanesulfonamidoethylaniline, particularly 3-methyl-4-amino-N-ethyl-N-β-methanesulfonamidoethylaniline, are preferred.

Aminophenol derivatives may also be used as a developing agent, such as o- or p-aminophenol, 4-amino-2-methylphenol, 2-amino-3-methylphenol, 2-hydroxy-3-amino-1,4-dimethylbenzene, etc.

In addition, color developing agents described in L. F. A. Mason, *Photographic Processing Chemistry*, pp. 226 to 229, Focal Press (1966), U.S. Pat. Nos. 2,193,015 and 2,592,364, and Japanese Patent Application (OPI) No. 64933/73 can also be employed. If necessary, these color developing agents may be used in combinations of two or more thereof.

The processing temperature for color development preferably ranges from 3° to 50° C., more preferably from 33° to 45° C. From the standpoint of solution stability, etc., the color developing solution preferably has a pH of 12 or less, and more preferably 11.0 or less.

The color developing solution to be used in the invention may contain benzyl alcohol as a development accelerator, but preferably, it does not substantially contain benzyl alcohol. What the color developing solution does not substantially contain benzyl alcohol means that the color developing solution contains not higher than 2 ml/l and preferably not higher than 0.5 ml/l of benzyl alcohol and that, most preferably, it does not at all contain benzyl alcohol. Further, the color developing solution may contain various compounds other than benzyl alcohol. For example, there can be exemplified various dyes (e.g., phenosafranine), and neutral salts (e.g., thallium nitrate, potassium nitrate, etc.) as described, e.g., in U.S. Pat. No. 2,648,604, Japanese Patent Publication No. 9503/69, and U.S. Pat. No. 3,171,247; nonionic compounds such as polyethylene glycol and derivatives thereof, polythioethers, etc., as described, e.g., in U.S. Pat. Nos. 2,533,990, 2,531,832, 2,950,970 and 2,577,127; thioether compounds as described in U.S. Pat. No. 3,201,242; and compounds described in Japanese Patent Application (OPI) Nos. 156934/83 and 220344/85.

In carrying out development in a short time as in the present invention, not only a means for acceleration of development but also a means for prevention of developer fog would be important subjects to consider. Antifoggants which are preferably applicable to the present invention include alkali metal halides, e.g., potassium bromide, sodium bromide, potassium iodide, etc.; and organic antifoggants, such as nitrogen-containing heterocyclic compounds (e.g., benzotriazole, 6-nitrobenzimidazole, 5-nitrosoindazole, 5-methylbenzotriazole, 5-nitrobenzotriazole, 5-chlorobenzotriazole, 2-thiazolylbenzimidazole, 2-thiazolylmethylbenzimidazole, hydroxyazaindolizine, etc.), mercapto-substituted heterocyclic compounds (e.g., 1-phenyl-5-mercaptotetrazole, 2-mercaptobenzimidazole, 2-mercaptobenzothiazole, etc.), and mercapto-substituted aromatic compounds (e.g., thiosalicylic acid, etc.). Preferred of these are halides. It does not matter if these antifoggants are eluted from color light-sensitive materials during processing and accumulated in the developer.

The color developing solution to be used in the invention can further contain various additives: pH buffering agents, e.g., alkali metal carbonates, borates, or phosphates, etc.; preservatives, e.g., hydroxylamine, triethanolamine, compounds described in West German Patent Application (OLS) No. 2622950, sulfites, bisulfites, etc.; organic solvents, e.g., diethylene glycol, etc.; dye forming couplers; competing couplers; nucleating agents, e.g., sodium boron hydride, etc.; auxiliary developing agents, e.g., 1-phenyl-3-pyrazolidone, etc.; thickening agents; chelating agents, such as aminopolycarboxylic acids (e.g., ethylenediaminetetraacetic acid, nitrilotriacetic acid, cyclohexanediaminetetraacetic acid, iminodiacetic acid, N-hydroxymethylethylenediaminetriacetic acid, diethylenetriaminepentaacetic acid, triethylenetetraminehexaacetic acid, and the compounds described in Japanese Patent Application (OPI) No. 195845/83), 1-hydroxyethylidene-1,1'-diphosphonic acid, the organic phosphonic acids described in *Research Disclosure*, RD No. 18170 (May 1979), aminophosphonic acids (e.g., aminotris(methylenephosphonic acid), ethylenediamine-N,N,N',N'-tetramethylenephosphonic acid, etc.), and phosphonocarboxylic acids (e.g., those described in Japanese patent Application (OPI) Nos. 102726/77, 42730/78, 121127/79, 4024/80, 4025/80, 126241/80, 65955/80, and 65956/80, and *Research Disclosure*, RD No. 18170 (May 1979); and the like.

However, it is preferred that the color developing solution is free from at least one of diethylhydroxylamine and triethanolamine, more preferably both of them.

If desired, the color development bath may be ddivided into two or more, and the first or the last bath is replenished with a color developer replenisher to thereby make reduction in developing time and amount of the replenisher.

After color development, silver halide color light-sensitive materials are usually subjected to bleaching. Bleaching may be carried out simultaneously with fixation (bleach-fixing), or these two steps may be effected separately. Bleaching agents to be used include compounds of polyvalent metals, e.g., iron (III), cobalt (III), chromium (VI), copper (II), etc., peracids, quinones, nitroso compounds, etc. Examples of the bleaching agents are ferricyanides; bichromates; organic complex salts of iron (III) or cobalt (III), such as those formed with aminopolycarboxylic acids (e.g., ethylenediaminetetraacetic acid, diethylenetriaminepentaacetic acid, nitrilotriacetic acid, 1,3-diamino-2-propanoltetraacetic acid, etc.), or organic acids (e.g., citric acid, tartaric acid, malic acid, etc.); persulfates, manganates; nitrosophenol, etc. Particularly preferred among them are potassium ferricyanide, sodium (ethylenediaminetetraacetato)iron (III), ammonium (ethylenediaminetetraacetato)iron (III), ammonium (triethylenetetraminepentaacetato)iron (III), and persulfates. (Ethylenediaminetetraacetato)iron (III) complex salts are useful in both an independent bleaching bath and a bleach-fixing monobath.

The bleaching bath or bleach-fixing bath may contain various accelerators, if desired. The accelerators to be used include a bromine ion, an iodine ion, as well as thiourea compounds as described in U.S. Pat. No. 3,706,561, Japanese Patent Publication Nos. 8506/70 and 26586/84, and Japanese Patent Application (OPI) Nos. 32735/78, 36233/78, and 37016/78; thiol compounds as described in Japanese Patent Application (OPI) Nos. 124424/78, 95631/78, 57831/78, 32736/78, 65732/78, and 52534/79, and U.S. Pat. No. 3,893,858; heterocyclic compounds as described in Japanese Patent Application (OPI) Nos. 59644/74, 140129/75, 28426/78, 141623/78, 104232/78 and 35727/79; thioether compounds as described in Japanese Patent Application (OPI) Nos. 20832/77, 25064/80, and 26506/80; quaternary amines as described in Japanese Patent Application (OPI) No. 84440/83; thiocarbamoyl compounds as described in Japanese Patent Application (OPI) No. 42349/84; and the like.

Fixing agents to be used include thiosulfates, thiocyanates, thioether compounds, thioureas, a large amount of iodides, etc., with thiosulfates being widely employed. Preservatives for the bleach-fixing bath or fixing bath preferably include sulfites, bisulfites, and carbonylbisuflite addition products.

Bleach-fixing or fixation is usually followed by washing with water. For the purpose of preventing sedimentation or saving water, a washing bath can contain various known compounds according to necessity. Such compounds include water softeners for preventing sedimentation, e.g., inorganic phosphoric acids, aminopolycarboxylic acids, organic phosphoric acids, etc.; bactericides or anti-molds for preventing growth of various bacteria, algae or fungi; hardeners, e.g., magnesium salts, aluminum salts, etc.; surface active agents for reducing a drying load or preventing unevenness, and the like. The compounds described in L. E. West, *Photo. Sci. and Eng.*, Vol. 9, No. 6 (1965) may also be added. In particular, addition of chelating agents and anti-molds is effective. Water saving can be achieved by carrying out washing in a multi-stage (e.g., 2 to 5 stages) countercurrent system.

The washing step may be followed by or replaced with a multi-stage countercurrent stabilization step as described in Japanese Patent Application (OPI) No. 8543/82. The stabilizing step requires from 2 to 9 vessels arranged in a countercurrent system. The stabilizing bath contains various additives for image stabilization, such as buffering agents for film pH-adjustment (e.g., borates, metaborates, borax, phosphates, carbonates, potassium hydroxide, sodium hydroxide, aqueous ammonia, monocarboxylic acids, dicarboxylic acids, polycarboxylic acids, etc.), and formalin. If desired, the stabilizing bath can further contain water softeners (e.g., inorganic or organic phosphoric acids, aminopolycarboxylic acids, aminopolyphosphonic acids, phosphonocarboxylic acids, etc.), bactericides (e.g., Proxel®, isothiazolone, 4-thiazolylbenzimidazole, halogenated phenolbenzotriazoles, etc.), surface active agents, fluorescent brightening agents, hardeners, etc.

The stabilizing bath may furthermore contain, as film pH adjustors after processing, various ammonium salts, e.g., ammonium chloride, ammonium nitrate, ammonium sulfate, ammonium phosphate, ammonium sulfite, ammonium thiosulfate, etc.

The present invention will now be illustrated in greater detail with reference to the following examples, but it should be understood that the present invention is not limited thereto.

EXAMPLE 1

To 16.4 g of Coupler (M-1) were added 32 ml of a 1/1 (v/v) mixture of tris(2-ethylhexyl) phosphate and tricresyl phosphate and 32 ml of ethyl acetate, and the mixture was heated for dissolution. Then, the solution thus formed was added to 100 ml of an aqueous solution containing 10 g of gelatin and 1.0 g of sodium dodecylbenzenesulfonate, and the mixture was stirred at high speed to provide an emulsified dispersion of the coupler. The whole amount of the emulsified dispersion was added to 100 g (6.5 g of silver) of a silver chlorobromide emulsion containing 50 mole% bromide, and after adding thereto 10 ml of a 2% 2,4-dichloro-6-hydroxy-s-triazine sodium salt as a hardener, the emulsion was coated on a paper support, both surfaces of which were coated with polyethylene, at a silver coverage of 200 mg/m². Then, a gelatin layer was formed on the emulsion layer to provide Sample A.

Then, in place of Coupler (M-1), an equimolar amount of each of Couplers (M-7), (M-11), (M-15), (M-20), (M-26), (M-27), and (M-29) was taken, a mixture of tris(2-ethylhexyl) phosphate and tricresyl phosphate was added to the coupler in an amount of twice by volume (ml) corresponding the amount (g) of each coupler, and by following the same procedure as the case of Sample A, Samples B, C, D, E, F, G, and H were prepared, respectively.

Also, by following the same procedure as above using each of Comparative Couplers (1) to (5) shown below in place of the aforesaid coupler of this invention, Samples I, J, K, L, and M were prepared.

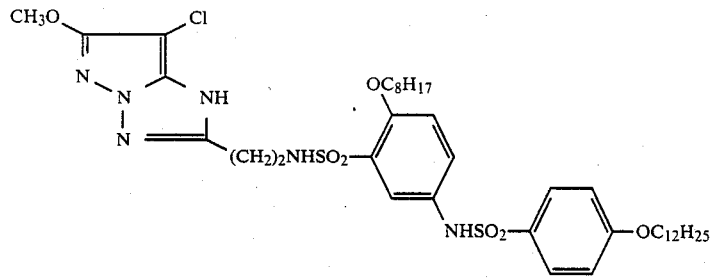

Comparative Coupler (1)

-continued

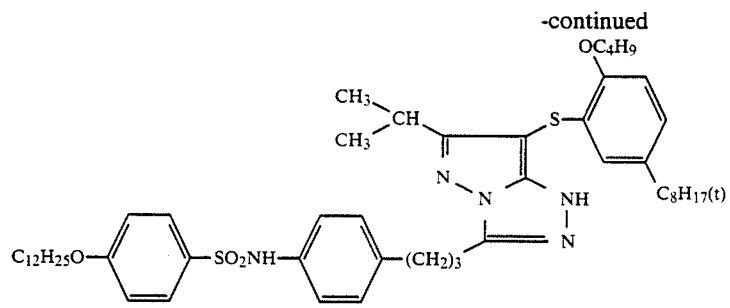

Comparative Coupler (2)

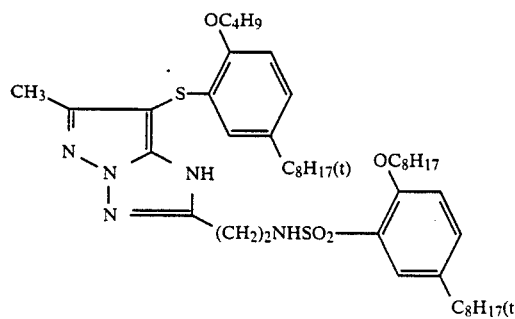

Comparative Coupler (3)

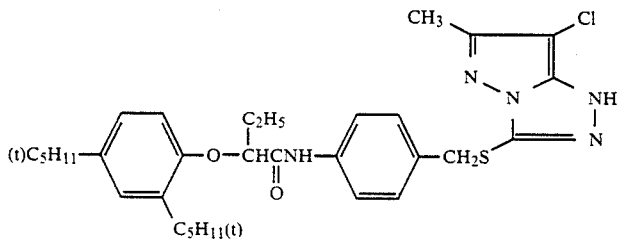

Comparative Coupler (4)

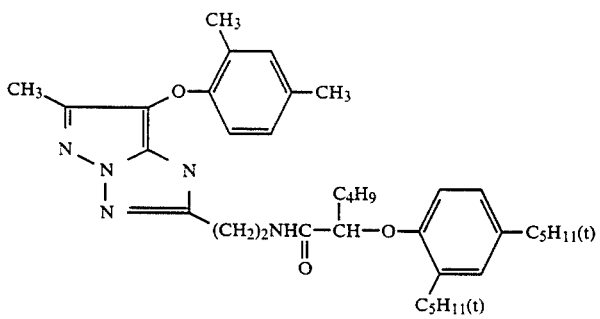

Comparative Coupler (5)

Each of the samples thus prepared was subjected to wedgewise exposure of 1,000 C.M.S., developed for 2 minutes by Processing (A) using Color Developing Solution (A) or Processing (B) using Color Developing Solution (B), bleach-fixed as indicated below, and then washed.

Then, the evaluation of the photographic properties of each color image obtained was performed with respect to the relative sensitivity, the maximum density (Dmax), and the fog density.

The relative sensitivity is indicated by a relative value when the sensitivity of Sample A in the case of developed with Color Developing Solution (A) (i.e., Processing (A)) was defined as 100. Also, the sensitivity was determined as a relative value of the reciprocal of an exposure amount necessary for providing a density of the minimum density plus 0.5. The results obtained are shown in Table I below.

The processing steps employed were as follows.

| Processing Step | Temperature | Time |
|---|---|---|
| Color Development | 38° C. | 2.0 min. |
| Bleach-fixing | 33° C. | 1.5 min. |
| Washing | 28 to 35° C. | 3.0 min. |

The compositions of the processing liquids used in the above process were as follows.

| Color Developing Solution (A): | |
|---|---|
| Nitrilotriacetic acid.3Na | 2.0 g |
| Benzyl alcohol | 15 ml |
| Diethylene glycol | 10 ml |
| Sodium sulfite | 2.0 g |
| Potassium bromide | 0.5 g |
| Hydroxylamine sulfate | 3.0 g |
| 4-Amino-3-methyl-N—ethyl-N—[β-(methanesulfonamido)ethyl]-p-phenylenediamine sulfate | 5.0 g |
| Sodium carbonate (monohydrate) | 30.0 g |

-continued

| Water to make | 1 liter (pH = 10.1) |
|---|---|
| Color Developing Solution (B): | |
| Nitrilotriacetic acid.3Na | 2.0 g |
| Sodium sulfite | 2.0 g |
| Potassium bromide | 0.5 g |
| Hydroxylamine sulfate | 3.0 g |
| 4-Amino-3-methyl-N—ethyl-N—[β-(methanesulfonamido)ethyl]-p-phenylenediamine sulfate | 5.0 g |
| Sodium carbonate (monohydrate) | 30.0 g |
| Water to make | 1 liter (pH = 10.1) |
| Bleach-Fixing Solution: | |
| Ammonium thiosulfate (54 wt %) | 150 ml |
| Sodium sulfite | 15 g |
| NH$_4$[Fe(III)(EDTA)] | 55 g |
| EDTA.2Na | 4 g |
| Water to make | 1 liter (pH = 6.9) |

EDTA: Ethylenediaminetetraacetic acid

TABLE I

| Sample No. | Processing (A) | | | Processing (B) | | |
|---|---|---|---|---|---|---|
| | Relative Sensitivity | G Dmax | D Fog | Relative Sensitivity | G Dmax | D Fog |
| A | 100 | 2.26 | 0.17 | 98 | 2.20 | 0.11 |
| B | 112 | 2.31 | 0.12 | 99 | 2.25 | 0.12 |
| C | 98 | 2.21 | 0.12 | 94 | 2.18 | 0.12 |
| D | 97 | 2.20 | 0.12 | 91 | 2.15 | 0.11 |
| E | 108 | 2.25 | 0.11 | 98 | 2.21 | 0.11 |
| F | 93 | 2.11 | 0.13 | 91 | 2.06 | 0.12 |
| G | 95 | 2.15 | 0.13 | 92 | 2.01 | 0.13 |
| H | 96 | 2.19 | 0.13 | 92 | 2.10 | 0.12 |
| I | 110 | 2.30 | 0.15 | 85 | 1.12 | 0.15 |
| J | 45 | 1.53 | 0.12 | 38 | 1.21 | 0.12 |
| K | 65 | 1.85 | 0.12 | 45 | 1.55 | 0.12 |
| L | 95 | 2.03 | 0.16 | 82 | 1.85 | 0.15 |
| M | 111 | 2.30 | 0.15 | 85 | 1.98 | 0.14 |

As is clear from the results shown in Table I above, it can be seen that in the case of using the magenta couplers in accordance with this invention, the photographic properties obtained using a color developing solution containing no benzyl alcohol do not largely change as compared with the case of developing using a color developing solution containing benzyl alcohol. Also, in the case of using a coupler that the pyrazoloazole nucleus has a substituent composed of an alkyl group only and has an arylthio split-off group, as in the comparative couplers, the lowering of coloring is severe when a color developing solution containing no benzyl alcohol is used. Also, in the case of using a coupler having a substituent other than arylthio split-off group, the formation of fog is great although the relative sensitivity and Dmax are recovered. From the results, it is clear that the magenta couplers for use in this invention are particularly excellent couplers.

Further, since the color developing solution used in this invention does not contain an organic amine usually used as a stabilizer, such as diethylhydroxylamine or triethanolamine, there are advantages that it is free from bromination of the amine in the processing and that generation of magenta color stain after the processing is small.

EXAMPLE 2

The yellow stain density ($D_B$) formed in unexposed areas of each of Samples A to M prepared as in Example 1 when the color print obtained from the sample through Processing (A) was stored for 4 days at 100° C. and also the reduction (reduction ratio indicated by %) of the magenta density ($D_G$) with respect to an initial density of 1.0 and yellow stain density ($D_B$) formed in unexposed areas when each sample was irradiated by a xenon fade-o-meter (100,000 lux) for 8 days were measured using a Macbeth RD-514 type densitometer.

The results obtained are shown in Table II below.

TABLE II

| Sample No. | $D_B$ (100° C., for 4 days) | Reduction in $D_G$ (Xe light irradiated for 8 days) | $D_B$ (Xe light irradiated for 8 days) |
|---|---|---|---|
| A | +0.03 | 8% | +0.02 |
| B | +0.03 | 11% | +0.02 |
| C | +0.04 | 9% | +0.03 |
| D | +0.05 | 15% | +0.02 |
| E | +0.03 | 6% | +0.02 |
| F | +0.06 | 20% | +0.03 |
| G | +0.05 | 19% | +0.03 |
| H | +0.05 | 19% | +0.02 |
| I | +0.21 | 21% | +0.04 |
| J | +0.11 | 51% | +0.04 |
| K | +0.08 | 19% | +0.03 |
| L | +0.08 | 49% | +0.03 |
| M | +0.09 | 22% | +0.03 |

As is clear from the results of Table II, it can be seen that in the case of using the magenta couplers for use in this invention, coloring of unexposed areas by light and heat is less than in the case of comparative couplers, and that the color images obtained the magenta couplers of the invention are excellent in light fastness.

EXAMPLE 3

A multilayer color photographic paper was prepared by forming layers having the composition shown below on a paper support having polyethylene coatings on both surfaces thereof. The coating compositions for the layers were prepared as follows.

Preparation of coating Composition for Layer 1:

In 10 ml of ethyl acetate and 4 ml of solvent (c) were dissolved 10 g of yellow coupler (a) and 2.3 g of dye image stabilizer (b), and the solution was dispersed by emulsification in 90 ml of an aqueous 10% gelatin solution containing 5 ml of 10% sodium dodecylbenzensulfonate. On the other hand, a blue-sensitizing dye shown below was added to a silver chlorobromide emulsion (silver bromide: 80 mole%, silver content: 70 g/kg) in an amount of $4.0 \times 10^{-4}$ mole per mole of silver chlorobromide to provide 90 g of a blue-sensitive silver halide emulsion. Then, the emulsified dispersion obtained above was mixed with the silver halide emulsion, and the concentration of gelatin was adjusted as shown in Table III below to provide a coating composition for Layer 1.

Coating compositions for Layers 2 to 7 were prepared according to the aforesaid manner. In addition, 1-oxy-3,5-dichloro-s-triazine sodium salt was used for each layer as a gelatin hardener.

The spectral sensitizer used for each silver halide emulsion was as follows.

For the Blue-Sensitive Emulsion Layer:

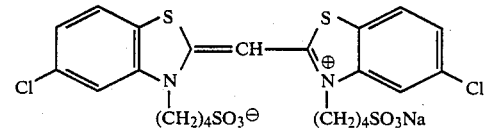

($4.0 \times 10^{-4}$ mole added per mole of silver halide).

For the Green-Sensitive Emulsion Layer:

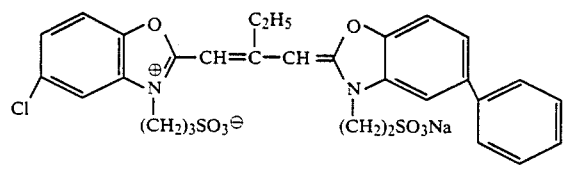

($3.0 \times 10^{-4}$ mole added per mole of silver halide).

For the Red-Sensitive Emulsion Layer:

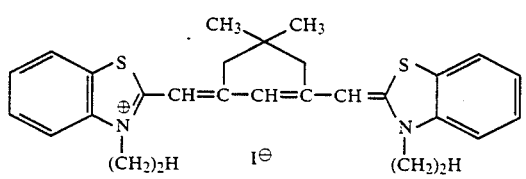

($1.0 \times 10^{-4}$ mole added per mole of silver halide).

As irradiation preventing dyes for each emulsion layer, the following dyes were used.

For the Green-Sensitive Emulsion Layer:

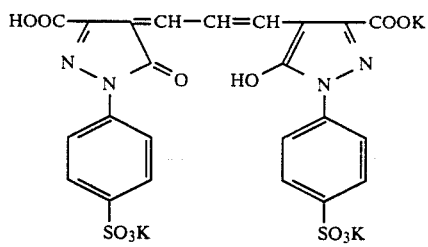

For the Red-Sensitive Emulsion Layer:

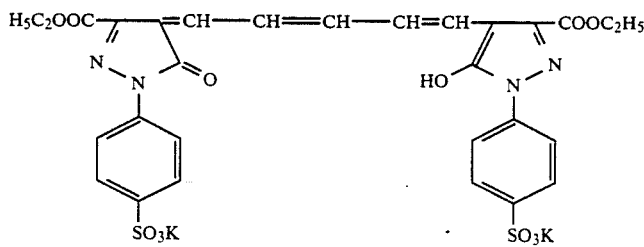

Other compounds used in this example were as follows.

(a) Yellow Coupler

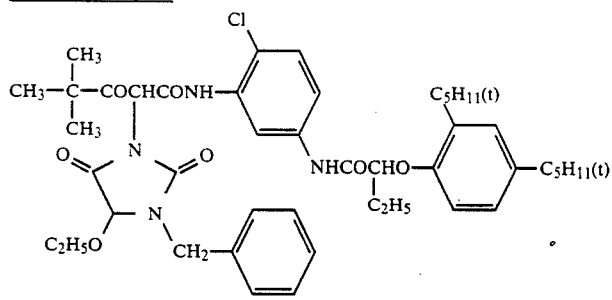

(b) Color Image Stabilizer

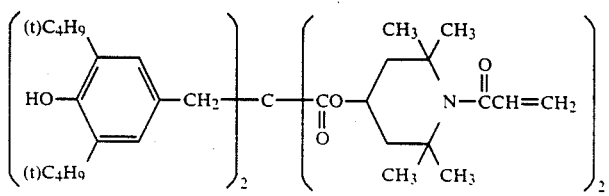

(c) Solvent

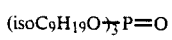
$(isoC_9H_{19}O)_3P=O$ (d) Color Mixing Preventing Agent

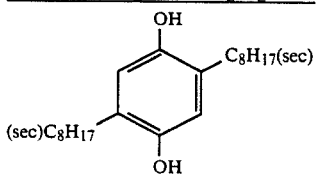

(e) Magenta Coupler
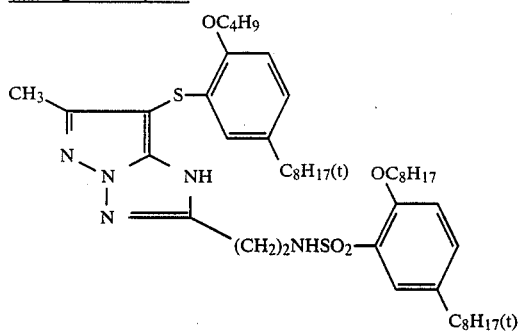
(Comparative Coupler (3))
(f) Color Image Stabilizer (f)
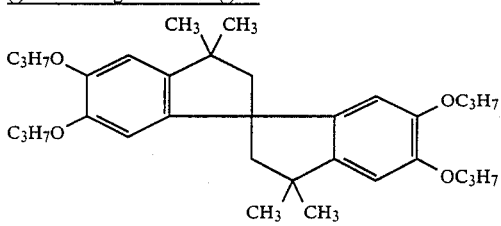
(g) Solvent
2:1 (by weight) mixture of
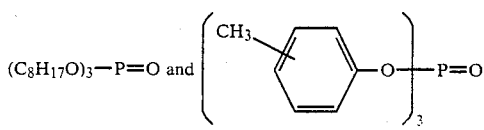
(h) Ultraviolet Absorbent
1:5:3 (by mole) mixture of
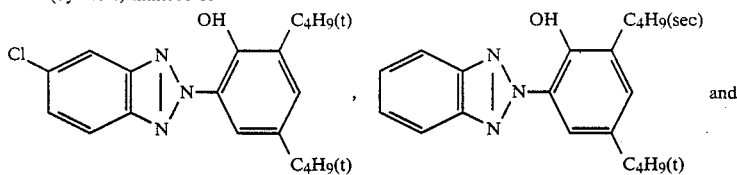
, and
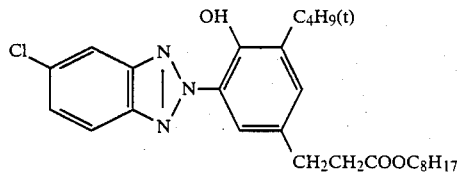
(i) Color Mixing Preventing Agent
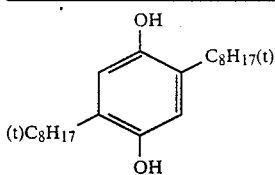
(j) Solvent
$(iso\ C_9H_{19}O)_3\!-\!P\!=\!O$
(k) Cyan Coupler
1:1 (by mole) mixture of

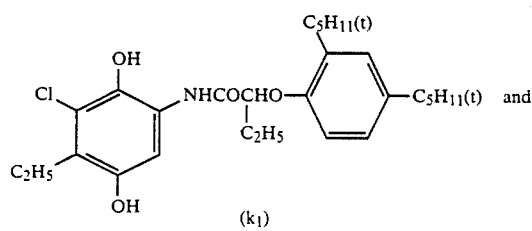

(k₁)

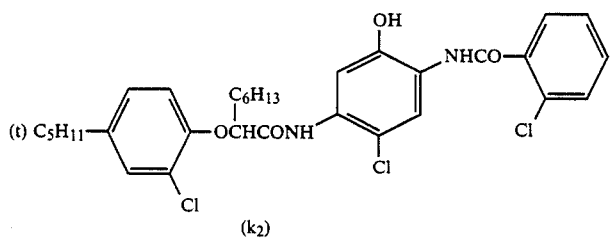

(k₂)

(l) Color Image Stabilizer
1:3:3 (by mole) mixture of

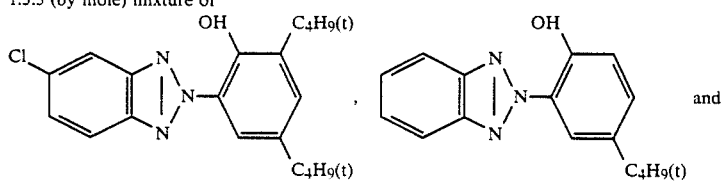 , 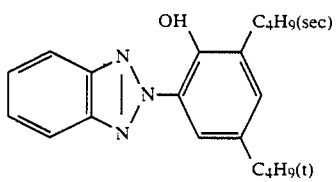 and

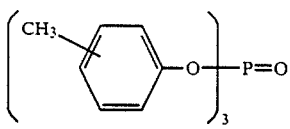

(m) Solvent $$\left[ \underset{CH_3}{\bigcirc} -O \right]_3 P=O$$

The layer structures were as follows. In addition, the support contained TiO₂, etc. as a white pigment and ultramarine blue as a bluish dye in the polyethylene coating at the emulsion side.

| Layer 1: Blue-Sensitive Emulsion Layer | |
|---|---|
| Silver chlorobromide emulsion (silver bromide: 80 mole %) | 0.35 g/m² as Ag |
| Gelatin | 1.35 g/m² |
| Yellow coupler (a) | 6.91 × 10⁻⁴ mole/m² |
| Color image stabilizer (b) | 0.13 g/m² |
| Solvent (c) | 0.02 g/m² |
| Layer 2: Color Mixing Preventing Layer | |
| Gelatin | 0.70 g/m² |
| Color mixing preventing agent (d) | 2.33 × 10⁻⁴ mole/m² |
| Layer 3: Green-Sensitive Emulsion Layer | |
| Silver chlorobromide emulsion (silver bromide: 75 mole %) | 0.15 g/m² as Ag |
| Gelatin | 1.56 g/m² |
| Magenta coupler (e) | 3.38 × 10⁻⁴ mole/m² |
| Color image stabilizer (f) | 0.17 g/m² |
| Solvent (g) | 0.57 g/m² |
| Layer 4: Ultraviolet Absorptive Layer | |
| Gelatin | 1.60 g/m² |
| Ultraviolet absorbent (h) | 1.70 × 10⁻⁴ mole/m² |
| Color mixing preventing agent (i) | 1.60 × 10⁻⁴ mole/m² |
| Solvent (j) | 0.27 g/m² |
| Layer 5: Red-Sensitive Emulsion Layer | |
| Silver chlorobromide emulsion (silver bromide: 70 mole %) | 0.22 g/m² as Ag |
| Gelatin | 0.90 g/m² |
| Cyan coupler (k) | 7.05 × 10⁻⁴ mole/m² |
| Color image stabilizer (l) | 5.20 × 10⁻⁴ mole/m² |
| Solvent (m) | 0.22 g/m² |
| Layer 6: Ultraviolet Absorptive Layer | |
| Gelatin | 0.54 g/m² |
| Ultraviolet absorbent (h) | 5.10 × 10⁻⁴ mole/m² |
| Solvent (j) | 0.08 g/m² |
| Layer 7: Protective Layer | |
| Gelatin | 1.33 g/m² |
| Acryl-modified copolymer of polyvinyl alcohol (modification degree: 17%) | 0.17 g/m² |

After balancing the surface tensions and viscosities of the coating compositions for Layers 1 to 7, the coating compositions were simultaneously coated on the support to provide Sample 101.

Then, by following the same procedure as above except that the couplers were changed as shown in Table III below, Samples 102 to 104 were prepared.

Each of the samples was subjected to gradation exposure for sensitometry and processed by the following steps.

| Processing Step | Temperature | Time |
|---|---|---|
| Color Development | 33° C. | 3.50 min. |
| Bleach-fixing | 33° C. | 1.50 min. |
| Washing | 24 to 34° C. | 3 min. |
| Drying | 80° C. | 1 min. |

The compositions of the processing liquids were as follows.

| Color Developing Solution | |
|---|---|
| Water | 800 ml |
| Diethylenetriaminepentaacetic acid | 3.0 g |
| Benzyl alcohol | 15 ml |
| Diethylene glycol | 10 ml |
| Sodium sulfite | 2.0 g |
| Potassium bromide | 0.5 g |
| Potassium carbonate | 30.0 g |
| N—Ethyl-N—($\beta$-methanesulfonamido-ethyl)-3-methyl-4-aminoaniline sulfate | 5.0 g |
| Hydroxylamine sulfate | 4.0 g |
| Fluorescent brightening agent (4,4'-stilbene series) | 1.0 g |
| Water to make | 1 liter |
| | (pH = 10.10 at 25° C.) |
| Bleach-Fixing Solution | |
| Water | 400 ml |
| Ammonium thiosulfate (70%) | 150 ml |
| Sodium sulfite | 18 g |
| Ethylenediaminetetraacetic acid iron (III) ammonium | 55 g |
| Disodium ethylenediaminetetraacetate | 5 g |
| Water to make | 1 liter |
| | (pH = 6.70 at 25° C.) |

TABLE III

| Sample No. | Coupler |
|---|---|
| 102 | Magenta Coupler (e) of Layer 3 was replaced with an equimolar amount of Coupler (M-1). |
| 103 | Magenta Coupler (e) of Layer 3 was replaced with an equimolar amount of Coupler (M-20). |
| 104 | Magenta Coupler (e) of Layer 3 was replaced with an equimolar amount of Coupler (M-27). |

The sensitivity, fog, and the maximum density (Dmax) of each of the samples were measured, and the results obtained are shown in Table IV.

TABLE IV

| Sample No. | Sensitivity | Fog ($D_G$) | Maximum Density ($D_G$) | Note |
|---|---|---|---|---|
| 101 | 45 | 0.09 | 1.14 | Comparison |
| 102 | 100 | 0.09 | 2.25 | Present Invention |
| 103 | 105 | 0.09 | 2.36 | Present Invention |
| 104 | 95 | 0.09 | 2.11 | Present Invention |

The sensitivity given above was shown by a relative value of the reciprocal of an exposure amount providing a density of 0.8, with that of Sample 102 being defined as 100.

As is clear from the results shown in Table IV, it can be seen that the magenta couplers for use in this invention give high sensitivity and high maximum density.

Thus, by using the magenta couplers for use in this invention, the high maximum color density is obtained at high coloring speed, and magenta color images having improved fastness are obtained. Also, even when a color developing solution containing substantially no benzyl alcohol is used in a short processing of shorter than 2 minutes and 30 seconds, magenta images having a high maximum color density can be obtained.

While the invention has been described in detail and with reference to specific embodiments thereof, it will be apparent to one skilled in the art that various changes and modifications can be made therein without departing from the spirit and scope thereof.

What is claimed is:

1. A color-image forming process which comprises developing with a color developing solution containing an aromatic primary amine developing agent and having substantially no benzyl alcohol a silver halide color photographic material containing a reflective support having thereon at least one silver halide emulsion layer associated with at least one pyrazoloazole coupler represented by formula (IIIb) or (IVb):

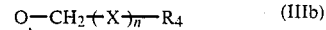
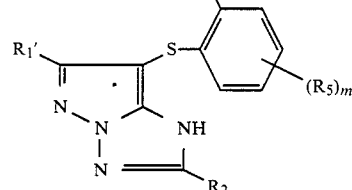

(IIIb)

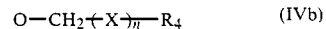
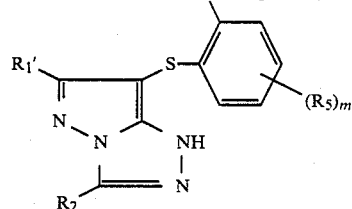

(IVb)

wherein $R_1'$ and $R_2$ each represents a substituent; at least one of said $R_1'$ and $R_2$ represents a group bonded to the pyrazoloazole nucleus by a nitrogen atom, oxygen atom, or sulfur atom thereof; X represents —CH$_2$O—, —CH$_2$O—CH$_2$CH$_2$O—, —CH$_2$SO$_2$—, —CH$_2$CH$_2$CH$_2$SO$_2$NH—, —CH$_2$CH$_2$CH$_2$SO$_2$NHCH$_2$CH$_2$O—, —CH$_2$CH$_2$CONH—, —CH$_2$COO—, —CH$_2$CONH—, —CH$_2$CH$_2$CONH—, —CH$_2$CH$_2$SO$_2$—, —CH$_2$CH$_2$SO$_2$NH—, —CH$_2$CH$_2$NHSO$_2$, —CH$_2$NHSO$_2$—, —CH$_2$NHCO—, —CH$_2$CH$_2$NHCO—,

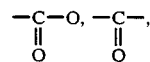

—SO$_2$—, —SO$_2$NH—,

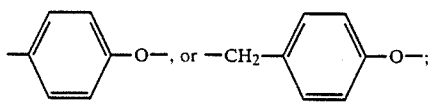

R₄ represents an alkyl group or an aryl group; R₅ represents a halogen atom, an alkoxy group, an alkyl group, an aryl group, a hydroxyl group, a cyano group, an amino group, an N-alkylamino group, an N,N-dialkylamino group, an N-anilino group, an acylamino group, a ureido group, an alkoxycarbonylamino group, an imido group, a sulfonamido group, a sulfamoylamino group, an alkoxycarbonyl group, a carbamoyl group, an acyl group, or an alkythio group; n represents 0 or 1; m represents 0 or an integer of 1 to 4; and when m is 2 or more, said $R_5$ groups may be the same or different, wherein the time for developing with said color developing solution is not longer than 2 minutes and 30 seconds.

2. A color image-forming process as in claim 1, wherein said aromatic primary amine developing agent is 3-methyl-4-amino-N-ethyl-N-β-hydroxyethylaniline or 3-methyl-4-amino-N-ethyl-N-β-methanesulfonamidoethylaniline.

3. A color image-forming process as in claim 2, wherein said aromatic primary amine developing agent is 3-methyl-4-amino-N-ethyl-N-β-methanesulfonamidoethylaniline.

4. A color image-forming process as in claim 1, wherein said color developing solution is free from at least one of diethylhydroxylamine and triethanolamine.

5. A color image-forming process as in claim 1, wherein the time for developing with said color developing solution is from 30 seconds to 130 seconds.

6. A color image-forming process as in claim 1, wherein
said group bonded to the pyrazoloazole nucleus by a nitrogen atom is an acylamino group, an alkoxycarbonylamino group, an aryloxycarbonylamino group, a sulfonamido group, an anilino group, a ureido group, a sulfamoylamino group, or an amino group;
said group bonded to the pyrazoloazole nucleus by an oxygen atom is an alkoxy group, an aryloxy group, a silyloxy group, or a heterocyclic oxy group; and
said group bonded to the pyrazoloazole nucleus by a sulfur atom is an alkylthio group, an arylthio group, or a heterocyclic thio group.

7. A color image-forming process as in claim 1, wherein one of $R_1$ and $R_2$ does not represent a group bonded to the pyrazoloazole nucleus by a a nitrogen atom, oxygen atom, or sulfur atom, and said group which is not bonded to the pyrazoloazole nucleus by a nitrogen atom, oxygen atom, or sulfur atom thereof is a group selected from a hydrogen atom, a halogen atom, an alkyl group, a heterocyclic group, and a cyano group.

8. A color image-forming process as in claim 1, wherein in formula (IIIb), $R_1'$ represents an alkoxy group, a ureido group, or an aryloxy group; and $R_2$ represents an alkyl group.

9. A color image-forming process as in claim 8, wherein n is 0; $R_4$ represents an unsubstituted alkyl group having from 1 to 7 carbon atoms; m is 1; and $R_5$ represents an unsubstituted alkyl group.

10. A color image-forming process as in claim 1, wherein in formula (IVb), $R_1'$ represents an alkyl group or an alkoxy group; and $R_2$ represents an alkylthio group.

11. A color image-forming process as in claim 10, wherein n is 0; $R_4$ represents an unsubstituted alkyl group having from 1 to 7 carbon atoms; m is 1; and $R_5$ represents an unsubstituted alkyl group.

12. A color image-forming process as in claim 1, wherein said silver halide color photographic material further contains a cyan coupler represented by formula (V) or (VI) and a yellow coupler represented by formula (VII)

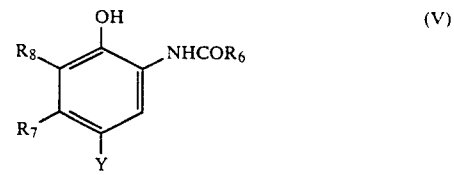

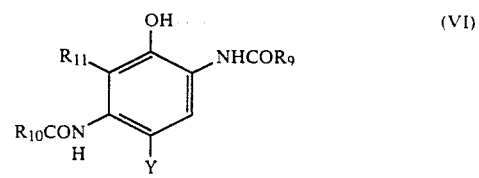

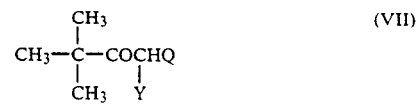

wherein $R_6$, $R_9$, and $R_{10}$ each represents an aliphatic group, an aromatic group, a heterocyclic group, an aromatic amino group, or a heterocyclic amino group; $R_7$ represents an aliphatic group; $R_8$ and $R_{11}$ each represents a hydrogen atom, a halogen atom, an aliphatic group, an aliphatic oxy group, or an acylamino group; Y represents a split-off group; Q represents a substituted or unsubstituted N-phenylcarbamoyl group; and in formulae (V) and (VI), said $R_7$ and $R_8$ or said $R_{10}$ and $R_{11}$ may be taken together to form a 5-, 6-, or 7-membered ring.

13. A color image-forming process as in claim 1, wherein said compound represented by formula (IIIb) or (IVb) is incorporated in a silver halide emulsion layer of said silver halide color photographic material in an amount from 0.1 to 0.5 mol per mol of silver halide in the emulsion layer.

* * * * *